US011779618B2

(12) United States Patent
Mattey et al.

(10) Patent No.: US 11,779,618 B2
(45) Date of Patent: Oct. 10, 2023

(54) TREATMENT OF TOPICAL AND SYSTEMIC BACTERIAL INFECTIONS

(71) Applicant: FIXED PHAGE LIMITED, Glasgow Strathclyde (GB)

(72) Inventors: Michael Mattey, Glasgow Strathclyde (GB); Emma Lisa Bell, Glasgow Strathclyde (GB)

(73) Assignee: FIXED PHAGE LIMITED, Glasgow (GB)

( * ) Notice: Subject to any disclaimer, the term of this patent is extended or adjusted under 35 U.S.C. 154(b) by 0 days.

(21) Appl. No.: 17/303,926

(22) Filed: Jun. 10, 2021

(65) Prior Publication Data

US 2021/0290703 A1 Sep. 23, 2021

Related U.S. Application Data

(60) Continuation of application No. 16/949,091, filed on Oct. 13, 2020, now abandoned, which is a continuation of application No. 16/532,137, filed on Aug. 5, 2019, now abandoned, which is a division of application No. 15/117,076, filed as application No. PCT/EP2015/052635 on Feb. 9, 2015, now abandoned.

(30) Foreign Application Priority Data

Feb. 7, 2014 (GB) ..................................... 1402139

(51) Int. Cl.
| | | |
|---|---|---|
| A61K 35/76 | (2015.01) | |
| A61K 47/69 | (2017.01) | |
| A61K 9/00 | (2006.01) | |
| A61K 9/06 | (2006.01) | |
| A61K 31/43 | (2006.01) | |
| A61K 47/34 | (2017.01) | |
| C12N 7/00 | (2006.01) | |

(52) U.S. Cl.
CPC ............ *A61K 35/76* (2013.01); *A61K 9/0014* (2013.01); *A61K 9/06* (2013.01); *A61K 31/43* (2013.01); *A61K 47/34* (2013.01); *A61K 47/6927* (2017.08); *C12N 7/00* (2013.01); *C12N 2795/00032* (2013.01); *C12N 2795/00033* (2013.01); *C12N 2795/10132* (2013.01)

(58) Field of Classification Search
CPC ........ A61K 35/76; A61K 9/0014; A61K 9/06; A61K 31/43; A61K 47/34; A61K 47/6927; C12N 7/00; C12N 2795/00032; C12N 2795/10132
See application file for complete search history.

(56) References Cited

U.S. PATENT DOCUMENTS

| 2002/0001590 A1 | 1/2002 | Kelly et al. |
| 2003/0180319 A1 | 9/2003 | Rapson et al. |
| 2007/0014770 A1 | 1/2007 | Holland et al. |

FOREIGN PATENT DOCUMENTS

| EP | 0414304 A2 | 2/1991 | |
| WO | WO 2003/080823 A2 | 10/2003 | |
| WO | WO 2003/093462 A2 | 11/2003 | |
| WO | WO-03093462 A2 * | 11/2003 | ............. A61K 35/76 |
| WO | WO-2006047872 A1 * | 5/2006 | ........... A23K 20/195 |
| WO | WO 2006/060171 A2 | 6/2006 | |
| WO | WO 2007/072049 A2 | 6/2007 | |
| WO | WO 2009/108964 A2 | 9/2009 | |
| WO | WO 2012/175749 A1 | 12/2012 | |
| WO | WO 2014/049008 A1 | 4/2014 | |

OTHER PUBLICATIONS

Bruggermann et al.: ("Bacteriophages Infecting Propionibacterium acnes", Biomedresearch International, vol. 1, No. 2, Jan. 1, 2013 (Jan. 1, 2013), pp. 3-10, of record). (Year: 2013).*
Bowler et al., "Wound Microbiology and Associated Approaches to Wound Management," *Clinical Microbiology Reviews*, 14(2): 244-269 (2001).
Bruggemann et al., "Bacteriophages Infecting Propionibacterium acnes," *BioMed Research International*, vol. 1, Article ID 705741, 10 pages (2013).
Bruttin et al., "Human Volunteers Receiving *Escherichia coli* Phage T4 Orally: a Safety Test of Phage Therapy," *Antimicrobial Agents and Chemotherapy*, 49(7): 2874-2878 (Jul. 2005).
Brzin "Studies on the Corynebacterium acnes," *Acta Pathologica et Microbiologica Scandinavica*, vol. 60, pp. 599-608 (1964).
Capparelli et al., "Experimental Phage Therapy against *Staphylococcus aureus* in Mice," *Antimicrobial Agents and Chemotherapy*, 51(8): 2765-2773 (Aug. 2007).
Castillo et al. "Propionibacterium (Cutibacterium) acnes Bacteriophage Therapy in Acne: Current Evidence and Future Perspectives" *Dermatol Ther* (*Heidelb*) 9:19-31 (2019).
Gill et al., "Phage Choice, Isolation, and Preparation for Phage Therapy," *Current Pharmaceutical Biotechnology*, 11: 2-14 (2010).
Gilmer et al., "Novel Bacteriophage Lysin with Broad Lytic Activity Protects against Mixed Infection by *Streptococcus pyogenes* and Methicillin-Resistant *Staphylococcus aureus*," *Antimicrobial Agents and Chemotherapy* 57(6):2743-2750 (2013).

(Continued)

*Primary Examiner* — Snigdha Maewall
(74) *Attorney, Agent, or Firm* — FINNEGAN, HENDERSON, FARABOW, GARRETT & DUNNER, LLP

(57) ABSTRACT

Bacteriophage covalently attached to a carrier particle with an average diameter of from 0.1 microns to 15 microns, are used in topical treatment of bacterial infection. Bacteriophage covalently attached to a carrier particle of average diameter 7 microns or less are used in systemic treatment of bacterial infection. A plurality of bacteriophages lytic against different bacterial strains gives wide antibacterial activity. A combination therapy comprises administration of antibiotic and bacteriophage covalently attached to a carrier particle.

12 Claims, 12 Drawing Sheets

(56) References Cited

OTHER PUBLICATIONS

International Search Report and Written Opinion of the International Searching Authority for International Patent Application No. PCT/EP2015/052635 dated Sep. 30, 2015, from the European Patent Office.
Jończyk-Matysiak et al., "Prospects of Phage Application in the Treatment of Acne Caused by Propionibacterium acnes," *Frontiers in Microbiology*, vol. 8, Article 164: 1-11 (2017).
Kucharewicz-Krukowska et al., "Immunogenic Effect of a Bacteriophage in Patients Subjected to Phage Therapy," *Archivum Immunologiae Et Therapiae Experimentalis*, 35(5): 553-561 (1987).
Mattey et al., "Bacteriophage therapy—cooked goose or Phoenix rising?," *Current Opinion in Biotechnology*, 19:608-612 (2008).
Patents Act 1977: Search Report under Section 17(5) for corresponding GB Patent Application No. GB 1402139.8 dated Aug. 14, 2014, from the GB Intellectual Property Office.
Patents Act 1977: Search Report under Section 17(6) for corresponding GB Patent Application No. GB 1402139.8 dated Sep. 11, 2014, from the GB Intellectual Property Office.
Skurnik et al., "Phage therapy: Facts and fiction," *International Journal of Medical Microbiology*, 296: 5-14 (2006).
Southwick, "Infectious Diseases, A Clinical Short Course" Second edition, 2007, Chapter 10—Skin and Soft Tissue Infections, p. 256-272, McGraw-Hill Companies.
Sulakvelidze et al., "Bacteriophage Therapy," *Antimicrobial Agents and Chemotherapy*, 45(3): 649-659 (Mar. 2001).
Troccaz et al. Mapping axillary microbiota responsible for body odours using a culture-independent approach *Microbiome* 3:3 (2015).
Gupta, S. et al., "Cutaneous Surgical Wounds Have Distinct Microbiomes from Intact Skin", Microbiology Spectrum, vol. 11, No. 1, (Jan./Feb. 2023), 6 pages.
Kasman, L. M. et al., "Bacteriophages", NCBI Bookshelf, StatPearls [Internet], Treasure Island, Florida, StatPearls Publishing, (2022), 4 pages.
Mccallin, S. et al., "Current State of Compassionate Phage Therapy", Viruses, vol. 11, No. 343, (2019), 14 pages.
Oron, A., "BiomX Reports Topline Results of Phase 2 Cosmetic Acne Study", BiomX Press Release—Branford, Connecticut and Ness Ziona, Israel, (Oct. 18, 2021), 3 pages.
Silva, J. B. et al., "Host receptors for bacteriophage adsorption", FEMS Microbiology Letters, vol. 363, No. 4, (2016), 11 pages.
Tagami, H., "Location-related differences in structure and function of the stratum corneum with special emphasis on those of the facial skin", International Journal of Cosmetic Science, vol. 30, (2008), pp. 413-434.
Vandenheuvel, D. et al., "Bacteriophage Therapy: Advances in Formulation Strategies and Human Clinical Trials", Annu. Re. Viol., vol. 2, (2015), pp. 599-618.
Wagner et al., "virus", Encyclopaedia Britannica, https:/www.britannica.com/science/virus, Encyclopaedia Britannica, Inc. Publisher, Date Published: Jan. 5, 2023, (2022), 33 pages.

\* cited by examiner

TREATMENT OF TOPICAL AND SYSTEMIC BACTERIAL INFECTIONS

This application is a continuation of U.S. patent application Ser. No. 16/949,091, filed Oct. 13, 2020, which is a continuation of U.S. patent application Ser. No. 16/532,137, filed Aug. 5, 2019, which is a divisional of U.S. patent application Ser. No. 15/117,076, filed Aug. 5, 2016, which is a national stage application under 35 U.S.C. § 371 of International Application No. PCT/EP2015/052635, filed Feb. 9, 2015, which designated the U.S. and which claims the benefit under 35 U.S.C. § 119 of GB 1402139.8, filed Feb. 7, 2014, all of which are incorporated herein by reference.

FIELD OF THE INVENTION

The present invention relates to compositions and methods for treatment of bacterial infections in mammals, especially in humans. In particular, the present invention relates to treatment of topical bacterial infections and systemic bacterial infections.

BACKGROUND TO THE INVENTION

In recent years, as resistance to conventional antibiotics has continued to grow and the application of chemical biocides becomes increasingly unacceptable on environmental grounds, attention has turned to alternative methods for control of bacterial infection.

One promising approach involves the application of bacteriophages, being naturally occurring ubiquitous viruses that are harmless to humans, animals, plants and fish but lethal for bacteria. Bacteriophages are specific and will infect only particular bacterial types, with several sanitation products now on the market against pathogens such as *Salmonella* and *Listeria*.

Bacteriophages have specific actions against a range of strains of a single host species, occasionally more than one host species (e.g. *Escherichia* and *Klebsiella*). This makes bacteriophages less useful as general antibiotics, but more useful for targeted interventions. Antibiotics have wider specificity and are therefore useful for non-targeted interventions and emergency use, but suffer from resistant strain emergence with use.

Topical infections such as acne and impetigo may be treatable with bacteriophage as an alternative to existing products that are regarded as inefficient: some hospital handwashes have been proposed that contain bacteriophage K but have not been widely pursued; many acne treatments are known but most include active agents such as salicylic acid and benzoyl peroxide known to damage the skin.

US 2007-014770 discloses a bacteriophage capable of lysing an anti-acne bacterium and a pharmaceutical composition comprising such a bacteriophage. US 2003-180319 discloses pharmaceutical compositions comprising a panel of bacteriophages, optionally in combination with a pharmaceutically acceptable carrier. The bacteriophages are disclosed as suitable to be incorporated into consumables such as soap, hand or face creams, shaving creams and foams, dental floss, tooth powder, toothpaste, etc. EP 0414304 discloses a bactericidal composition in the form of a cream or a lotion, comprising an oil, an emulsifier, water and a bacteriophage capable of lysing *Propionibacterium acnes*, which is known to cause acne. EP 1504088 discloses topical treatment of bacterial infections using bacteriophage-containing compositions, including the treatment of acne and infected wounds. In particular EP 1504088 describes topical application of a phage solution to nostrils using cotton-wool buds, but no other formulations. Other purported treatments using similar compositions include: reduction of body odour by targeting odour-producing skin bacteria; and treatment of dental caries or gum disease by targeting *Streptococcus mutans, Bacteroides gingivalis* and/or *Haemophilus actinomycetemcomitans*.

One general problem with bacteriophage therapy, identified e.g. in the "Bacteriophage Therapy" minireview by Sulakvelidze et al, Antimicrobial Agents and Chemotherapy, March 2001, pp 649-659 is the absence of demonstration of efficacy of such preparations. Indeed, in the prior art mentioned above no working formulations or proof of principle are provided.

Bruttin and Brüssow (*Antimicrob Agent Chemother.* 2005 July; 49(7), pp 2874-2878) reported on a safety test of phage therapy of diarrhoea, concluding that oral phage application did not cause a decrease in total fecal *E. coli* counts, i.e. did not cure the diarrhoea.

Other problems identified by Sulakvelidze et al include the risk that rapid clearance of phage from the human body will reduce or negate possible effects, production of anti-phage antibodies in the patient, poor stability of phage in the body, the narrow host range of phages and insufficient purity of phage preparations.

Kucharewicz-Krukowska and Slopek (Arch Immunol Ther Exp (Warsaw) 1987; 35(5) pp 553-561) documented the production of antibodies following administration of free bacteriophage, detecting both neutralising and haemagglutinating antibodies. Another review, by Skurnik and Strauch (International Journal of Medical Microbiology 296 (2006) pp 5-14) noted that the in vivo susceptibility of bacterial pathogens to bacteriophages is still largely poorly understood. Lastly, Capparelli et al (Antimicrobial Agents and Chemotherapy, August 2007, pp 2765-2773) described a phage therapy against *S. aureus*, using a phage dose of $10^9$ PFU, thus requiring an exceptionally high, and off-putting, quantity of phage to achieve therapy in mice.

WO 03/093462 (University of Strathclyde) and WO 2012/175749 (Fixed Phage) disclose particles with bacteriophage covalently linked thereto for treatment of bacterial infection. WO 03/093462 discloses ingesting a preparation containing bacteriophage covalently immobilised on 10 μm beads for the treatment of food poisoning. It does not disclose the use of beads of any other size. WO 2012/175749 discloses the application of a preparation containing bacteriophage immobilised on particles for the treatment of infected deep wounds and bacterial infection of plants.

Neither WO 2012/175749 nor WO 2012/175749 disclose application of preparations comprising particles bearing covalently immobilised bacteriophage to the skin or external surface of a human or animal patient.

WO 2007/072049 (Blaze Venture Technologies) discloses methods of stabilising bacteriophage by covalently linking them to particles of 10 μm in diameter by means of activating the particles with an electrical discharge.

US 2002/001590 (Kelly) discloses bacteriophage capable of lysing methicillin-resistant *Staphylococcus aureus* (MRSA) and pharmaceutical compositions comprising such bacteriophage.

An aim of the present invention is to provide compositions that are active in treatment of topical bacterial infections. Another aim is to provide compositions that are systemically active in treatment of bacterial infections. In specific embodiments the aims include treatment of such infections in humans.

SUMMARY OF THE INVENTION

Accordingly, the present invention provides bacteriophage covalently attached to a carrier particle, for use in topical treatment of bacterial infection.

Topical formulations, comprising bacteriophage covalently attached to a carrier particle and a pharmaceutically acceptable carrier or excipient, are also provided for treatment of bacterial infection, as are methods of treating such infections.

The invention further provides bacteriophage covalently attached to a carrier particle of average diameter 7 microns or less, for use in systemic treatment of bacterial infection and compositions for systemic administration to a mammal to treat a bacterial infection, comprising the bacteriophage covalently attached to the carrier particle. Compositions of the invention may also contain an antibiotic, wherein the bacteriophage is lytic for bacteria against which the antibiotic is effective.

In all embodiments, the invention provides novel antibacterial therapies, methods and uses.

DETAILS OF THE INVENTION

The invention hence provides bacteriophage covalently attached to a carrier particle, for use in topical treatment of bacterial infection. In an example below, one such bacteriophage formulation showed significantly enhanced stability and activity retained over time compared to control formulations.

Preferred areas of the body for topical therapy using compositions of the invention include skin, teeth, eyes, nose and ears.

The carrier particle is typically approximately spherical. It may have an average diameter of up to 20 microns, up to 15 microns, up to 10 microns, from 0.1 microns, from 0.5 microns or any combinations of these—e.g. from 0.1 microns to 20 microns or from 0.5 microns to 10 microns. The particles in general can be approximately round or spheroid; they are preferably smooth, especially for use on sensitive parts of the body. In embodiments the bacteriophage is for use in treatment of bacterial infection of the skin.

Particle size of up to 20 microns gives a smoother feeling formulation (see e.g. creams described in more detail below), thus sizes in the range 1-20 microns, 10-15 microns, up to 10 microns and 1-10 microns are all suitable. Sizes around 3 microns give a particularly creamy feel to the formulation.

Particle size is suitably measured using methods and apparatus recognized as standard in the art. Particle sizing in dispersions can be accomplished using a variety of techniques, including laser diffraction, dynamic light scattering (DLS), disc centrifugation, and light microscopy. All of these techniques have their advantages and limitations. Laser diffraction relies on a well controlled presentation of the sample to the measurement region and is limited to samples with narrow range of particle concentrations. Dilution is often required and this may affect the particle size, particularly in compounds with high solubility. Examples of sizing equipment are made by Malvern Instruments (UK), using laser diffraction methods.

In further preferred embodiments of the invention, bacteriophages covalently attached to a plurality of particles are provided. These are preferably in relatively homogenous form, in which a large proportion, preferably substantially all, of the plurality of particles have diameters in the stated range, more preferably 80% or more, 90% or more or 95% or more of the particles with phage covalently attached have diameters in the stated range (being any range as set out above or elsewhere herein).

Particles for use in the invention to which bacteriophage are immobilised by covalent bonding are generally substantially inert to the animal to be treated. In examples, nylon particles (beads) were used. Other inert, preferably non-toxic biocompatible material may be used. In addition, the particle may be made of a biodegradable material. Suitable materials include polymethyl methacrylate, polyethylene, ethylene/acrylate copolymer, nylon-12, polyurethane, silicone resin, silica and nylon 1010. WO 2003/093462 describes further materials that the particles may be made from.

Immobilisation or attachment of bacteriophage to the particle substrate may be achieved in a number of ways. Preferably, bacteriophage are immobilised via covalent bonds formed between the bacteriophage coat protein and the carrier substrate.

Further, bacteriophage are preferably immobilised to the substrate via their head groups or nucleocapsid by activating the substrate particle before the addition and bonding of bacteriophage.

The term "activated/activating/activation" is understood to mean the activation of the substrate such as electrically, e.g. by corona discharge, or by reacting said substrate with various chemical groups (leaving a surface chemistry able to bind viruses, such as bacteriophage head or capsid groups).

Activation of said substrate may be achieved by, for example, preliminary hydrolysis with an acid, preferably HCl followed by a wash step of water and an alkali to neutralise the acid. Preferably, said alkali is sodium bicarbonate. Binding of bacteriophage via their head groups is advantageous. In the case of complex bacteriophage for example, binding via head groups leaves the tail groups, which are necessary for bacteria-specific recognition, free to infect, i.e., bind and penetrate a host bacterial cell. A plurality of various strain-specific bacteriophage may be immobilised to a substrate at any one time.

Coupling of phage to a substrate is as a result of the formation of covalent bonds between the viral coat protein and the substrate such as through an amino group on a peptide, for example a peptide bond. "Coupling Agents" that aid this process vary, and are dependent on the substrate used. For example, for coupling to the substrate nylon or other polymer with amino or carboxy surface groups the coupling agents carbodiimide or glutaraldehyde may be used.

Further details of methods and preferred methods for covalent attachment of bacteriophage to particles, retaining phage infectivity, are described in more detail in WO 2003/093462 and WO 2007/072049.

The invention is used to prepare topical treatments to be applied externally, e.g. to a patient's skin, teeth, eyes, nose and ears. In particular, the invention can be used for treatment of acne. One issue with known preparations is the presence of skin-harming chemicals. In particular embodiments of the invention, the bacteriophage is formulated free of salicylic acid and free of benzoyl peroxide.

The invention can also be used for treatment of (1) impetigo, e.g. caused by *S. aureus* and/or *S. pyogenes*; (2) folliculitis, furunculosis or carbunculosis, e.g. caused by *S. aureus* or *Pseudomonas aeruginosa*; (3) ecthyma, e.g. caused by *S. aureus* or *S. pyogenes*; or (4) erysipelas or cellulitis, e.g. caused by group A β-hemolytic *streptococcus* (erysipelas), *S. aureus* (cellulitis) or *S. pyogenes*.

The invention can also be used for treatment of bacteria responsible for body odours such as in a deodorant formulation or in an anti-perspirant formulation that also has deodorant properties.

It is preferred that multiple types of bacteriophage are used at the same time. This gives activity against more target bacteria and reduces development of resistance. Hence, embodiments of the invention comprise a plurality of bacteriophage active against 3 or more strains of bacteria, covalently attached to carrier particles, or bacteriophage active against 5 or more strains of bacteria, covalently attached to the carrier particles for use as described. Preferably the bacteriophages are all active against different strains of the same bacterial species, e.g. the bacteriophages are lytic for different strains of S. aureus or lytic for different strains of P. acnes.

The invention correspondingly provides a topical formulation, comprising bacteriophage covalently attached to a carrier particle as defined herein and a pharmaceutically acceptable carrier or excipient, for treatment of bacterial infection.

The topical formulation is preferably not simply bacteriophage on particles in suspension in water and preferably comprises a pharmaceutically acceptable carrier other than (optionally in addition to) water. The formulation may be in the form of a gel, cream or lotion, suitably comprising one or more or all of a gel-forming agent, a cream-forming agent, a wax, an oil, a surfactant and a binder. For topical use especially on skin, using one or more of these components can aid increasing the retention time on skin and increase effectiveness of the preparation.

Formulations as gel or creams are particularly preferred. In a specific embodiment of the invention, described in more detail below, a cream is prepared comprising bacteriophage covalently attached to nylon particles in an aqueous cream containing anhydrous lanolin, white soft paraffin BP and light liquid paraffin PhEur. In general, all creams and gels suitable for topical application to the skin, in particular to human skin, are suitable as base for the formulation of bacteriophage according to the invention.

Production of a cream or lotion in general requires the input of heat in order to mix and emulsify the composition. Application of heat is a useful way of reducing any contaminating bacterial load in such a standard composition. Native bacteriophage are susceptible to increased temperatures and become inactive upon heating and thus are unsuitable for inclusion during production of such preparations. However, surprisingly, bacteriophage covalently attached to a solid support are significantly more heat stable than native bacteriophage. Consequently, covalently immobilised bacteriophage can be included in heat-treated, e.g. heat-sterilised preparations. This is particularly advantageous because chemical- or radiation-based methods of sterilisation damage nucleic acids and thus are unsuitable for treatment of a bacteriophage-containing composition. Genetic material of the bacteriophage must remain intact for the bacteriophage to be infective.

Particular embodiments of the invention provide a cream or gel comprising bacteriophages lytic for P. acnes covalently attached to carrier particles of average diameter of up to 20 microns. The bacteriophages may be lytic for at least 3 or at least 5 or more different strains of P. acnes covalently attached to the carrier particles. These are especially suitable for acne or body odour (caused by bacteria) treatment.

Further particular embodiments of the invention provide a cream or gel comprising bacteriophages lytic for S. aureus covalently attached to carrier particles of average diameter of up to 20 microns. The bacteriophages may be lytic for at least 3 or at least 5 or more different strains of S. aureus covalently attached to the carrier particles. These are especially suitable for treatment of skin infections caused by S. aureus.

In use, it is found that phage immobilised onto particles, e.g. beads are more stable than free phage. In addition, the beads are found to bind to the skin, improving localisation and being less likely to be washed or brushed off or to fall off after drying of the formulation, again improving effectiveness of the therapy.

Still further provided by the invention are methods of treating a topical bacterial infection, comprising administering a bacteriophage covalently attached to a carrier particle or a formulation thereof as defined above.

Additionally provided by the present invention is bacteriophage covalently attached to a carrier particle of average diameter 7 microns or less, for use in systemic treatment of bacterial infection.

In a specific embodiment of the invention described in detail below, immobilised bacteriophages on such particles were used to treat a systemic S. aureus infection. The results showed that these systemically administered particles with bacteriophage covalently attached were safe and were effective in treating the infection.

Such bacteriophages on particles are hence adapted for use systemically, in that the carrier particles are at or below a chosen size to allow for circulation within blood vessels of the patient, in particular within a human patient. Similarly, carrier particles are suitably at or above a chosen size to prevent phagocytosis of the particles during circulation within the body of the patient, in particular within a human patient. The carrier particle may be approximately spherical and may separately have an average diameter of 6 microns or less, 5 microns or less, or 0.1 microns or more, 0.5 microns or more, 1 micron or more, or of from 0.1 microns to 6 microns, or from 1 micron to 5 microns.

As for the topical uses and formulations described herein, it is preferred that multiple types of bacteriophage are used at the same time. This gives activity against more target bacteria and reduces development of resistance. Hence, embodiments of the systemic treatment invention comprise a plurality of bacteriophage active against 3 or more strains of bacteria, covalently attached to carrier particles, or bacteriophage active against 5 or more strains of bacteria, covalently attached to the carrier particles. Preferably the bacteriophages are all active against different strains of the same bacterial species, e.g. the bacteriophages are lytic for staphylococci or for different strains of S. aureus or other systemically infecting bacteria.

In other embodiments, a bacteriophage of the invention is used in a combination therapy with antibiotics. Hence, the invention provides bacteriophage lytic for a bacterium covalently attached to a carrier particle of average diameter 7 microns or less in combination with antibiotic effective against the same bacterium, for use in treatment of systemic bacterial infection. Thus, in a specific embodiment of the invention set out below in more detail in the examples, a composition comprising both antibiotic at a therapeutically effective dose and bacteriophage covalently attached to carrier particles was effective in killing bacteria systemically, in blood and in organs throughout the body. The combination confirmed no adverse interaction between the respective components.

The combination is preferably for systemic administration to a mammal, especially humans. A suitable formulation, as used in examples below, is a formulation for intravenous or parenteral injection.

In the combination therapy, the carrier particles are suitably approximately spherical and suitably sized as described above, thus for example have an average diameter of 6 microns or less, or of from 0.1 microns to 6 microns, or 5 microns or less, or from 1 micron to 5 microns. The combination may use a plurality of bacteriophages active against 3 or more or 5 or more strains of bacteria, covalently attached to carrier particles. The bacteriophages may be lytic for staphylococci, especially for *S. aureus*.

In the combination therapy, the antibiotic is suitably administered at or above its minimum inhibitory concentration (MIC). In use, the bacteriophage present is lytic for and kills bacteria that are resistant to the antibiotic, improving the effectiveness of the therapy. In a specific example of the invention, described in more detail below, antibiotic was administered to bacteria known to have developed antibiotic resistance and hence the antibiotic was administered at below MIC, which would have been expected not to be effective against all bacteria. The antibiotic was administered in combination with phage, resulting in complete bacterial killing, thus demonstrating the effectiveness of the combination against resistant bacteria.

Compositions of the combination embodiment of the invention hence comprise the bacteriophage on particles and further comprise an antibiotic, wherein the bacteriophage is lytic for bacteria against which the antibiotic is effective.

Methods of the combination therapy, for systemic treatment of bacterial infection, comprise administering an antibiotic in combination with bacteriophage covalently attached to a carrier particle of average diameter 7 microns or less. Optional and preferred features of the methods are as described elsewhere herein in relation to systemic bacteriophage therapy.

The invention is suitable for use with bacteriophage in general, without limitation to the bacteriophage strain, though preferably with lytic bacteriophage.

Formulations of the invention comprise a therapeutically effective dose of bacteriophage against the target bacteria. The bacteriophage content will typically be from $10^2$-$10^{10}$ PFU, hence for liquid/gel type compositions $10^2$-$10^{10}$ PFU per ml, suitably $10^3$ PFU per ml or more and also separately suitably up to $10^9$ or up to $10^8$ PFU per ml.

The preferred formulations for topical treatments disclosed herein comprise a standard base and bacteriophage immobilised on beads as the active ingredient. Such preparations for topical use are consistent with those described in prior-published documents, including US 2003-180319 and EP 0414304, which are referred to above.

In particular formulations or compositions for topical use, the dose can be at low levels. The dose is optionally from $10^2$-$10^6$ PFU per ml. In use, this level of phage may achieve, on application to the skin, at least approximately 1 phage per $mm^2$ of skin, suitably up to 5, up to 10 or up to 100 phage per $mm^2$ of skin. Typically, when a topical infection is present direct application of the formulation means that a relatively low dose is effective; the juxtaposition of immobilised phage and infected area increases the probability of contact between phage and infecting bacteria. Also for topical use, the phage loading of the composition may be designed to deliver one phage per bead (thus, e.g. 1 phage per 5 micron bead) or from 1-5, from 1-10 or 1-100 phage per bead. Compositions may be designed therefore to comprise from $10^2$-$10^6$ particles per ml, from $10^2$-$10^5$ particles per ml or from $10^2$-$10^4$ particles per ml. In use, this bead level of phage may achieve, on application to the skin, at least approximately 1 particle per $mm^2$ of skin, suitably from 1-10 or from 1-100 particles per $mm^2$ of skin.

The preferred route for systemic administration of bacteriophage of the present invention is by injection, especially by intravenous delivery of a pharmaceutical preparation of bacteriophage covalently attached to particles, e.g. micro beads, as an active ingredient, suspended in a pharmaceutically acceptable carrier.

Systemic administration by injection is described in many publications including US 2002/001590, Sulakvelidze et al. (referred to above), Kucharewicz-Krukowska and Slopek (referred to above), and Skurnik and Strauch (referred to above). Therefore the methods of systemic treatment disclosed herein for compositions, methods and uses of the invention are consistent with methods of systemic treatment that are well known to the skilled person.

For systemic use, higher doses are generally required. A suitable dose of such formulations, e.g. for human use, may be in the range $10^5$-$10^{10}$ PFU or $10^7$-$10^{10}$ PFU or $10^7$-$10^9$ PFU. The particle preparation for these uses may be designed to deliver one phage per bead (thus, e.g. 1 phage per 5 micron bead) or from 1-5, from 1-10 or 1-100 phage per bead.

Bacteriophage for the invention include bacteriophage in general without limitation provided that the bacteriophage is obtainable and its host or target bacteria can be cultured and infected in culture. The bacteriophage can be ssRNA, dsRNA, ssDNA or dsDNA bacteriophage, with either circular or linear arrangement of the genetic material, and which infect cells of bacteria. The suitable bacteriophage include Myoviridae, Siphoviridae, Podoviridae, Lipothrixviridea, Rudiviridae, Ampullaviridae, Bacilloviridae, Bicaudaviridae, Clavaviridae, Corticoviridae, Cystoviridae, Fusseloviridae, Globuloviridae, Guttavirus, Inoviridae, Leviviridae, Microviridae, Plasmaviridae and Tectiviridae.

Examples of how to isolate desired phage are widespread in the literature, including just by way of illustration: Gill J J and Hyman P, "Phage choice, isolation, and preparation for phage therapy", *Curr Pharm Biotechnol.*, 2010, January; 11(1): pp 2-14, and the previously mentioned "Bacteriophage Therapy" minireview by Sulakvelidze et al., *Antimicrobial Agents and Chemotherapy*, March 2001, pp 649-659.

Advantages of the invention, attributable to one or more embodiments thereof, include increased activity, especially after medium to long term storage, resulting in increased product shelf-life. Similarly, an advantage of the invention is the increased resistance to heat of covalently immobilised bacteriophage included in products of the invention. Use of such heat-resistant bacteriophage simplifies the production and sterilisation process and thus makes compounding such preparations more efficient. Skin treatments can avoid harsh chemicals such as salicylic acid and benzoyl peroxide. Particle size is optionally small and can provide smooth feeling topical treatments. For systemic treatments, the achievement of systemic efficacy in the short term but also after many days post injection demonstrates long term retention of activity, including activity effectively stored in vivo on particles retained internally. Decreased clearance of phage on particles compared to free phage further prolongs the effectiveness of the therapy. Combining the specificity of bacteriophages to target antibiotic resistant strains of bacteria with the wider specificity of antibiotics may overcome known problems of antibiotic resistance, both in individual instances of use and in the environmental distribution of bacteria by providing a selection against particular resistance mechanisms.

Antibody responses to free phage are known from the prior art. In addition, it is appreciated in the art that using repeated doses of free bacteriophage will increase the likelihood of the production of neutralising antibodies which will be detrimental to the use of bacteriophage as an effective invasive therapy. According to the present invention, use of covalently immobilised bacteriophage has the surprising advantage of absent or very low stimulation of an antibody response. This is borne out in specific examples. Further, long term stability of immobilised preparations compared to free phage enables reduction in both the dose per administration and the number or frequency of administrations, leading to a further reduction in the immune response, if any, to the therapy. Immobilised bacteriophage may not generate an antibody response due to the fact there is little or no antigenic material on the surface of e.g. beads or microspheres to which phage is attached. This observation and the resultant advantage is unexpected and surprising. Using a human dose of, say $10^7$ to $10^{10}$ PFU (compare this with $10^9$ PFU of free phage used in the mouse prior art) is thus unlikely to produce an immune response even after repeated doses.

In specific embodiments of the invention, described in examples below, it is also found that phage immobilised onto particles are retained in the body, in active form, for long periods of time, by retention e.g. in the liver. Particles bearing active (i.e. infective) phage were detectable in the liver of animals 14 days after systemic injection. This provides a prolonged effect of the systemic treatment as blood circulating through the liver brings bacteria into contact with these trapped, active phage. The antibacterial activity is hence of unexpected and surprisingly long duration.

Phage may be separately neutralized by complement. Again, in separate specific testing of the invention, we have shown that surprisingly the immobilized phage is not neutralized by complement—whereas free phage is. This is a further and separate benefit of the uses and therapies of the invention.

The invention is now illustrated in specific embodiments with reference to the accompanying drawings, in which FIG. 1 shows the survival of phage in phage-containing formulations of the invention in storage;

Figure 6:
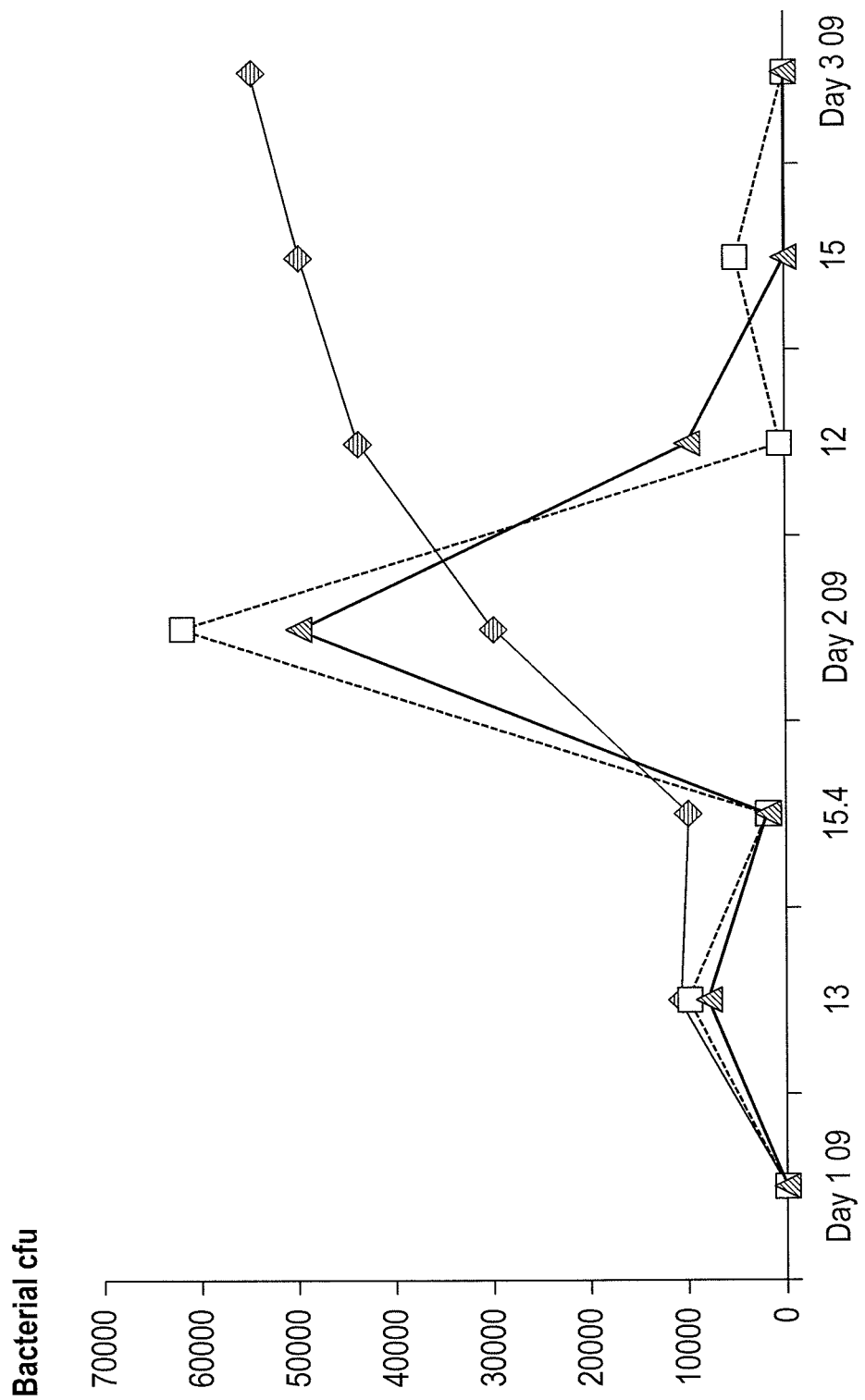
Figure 7:
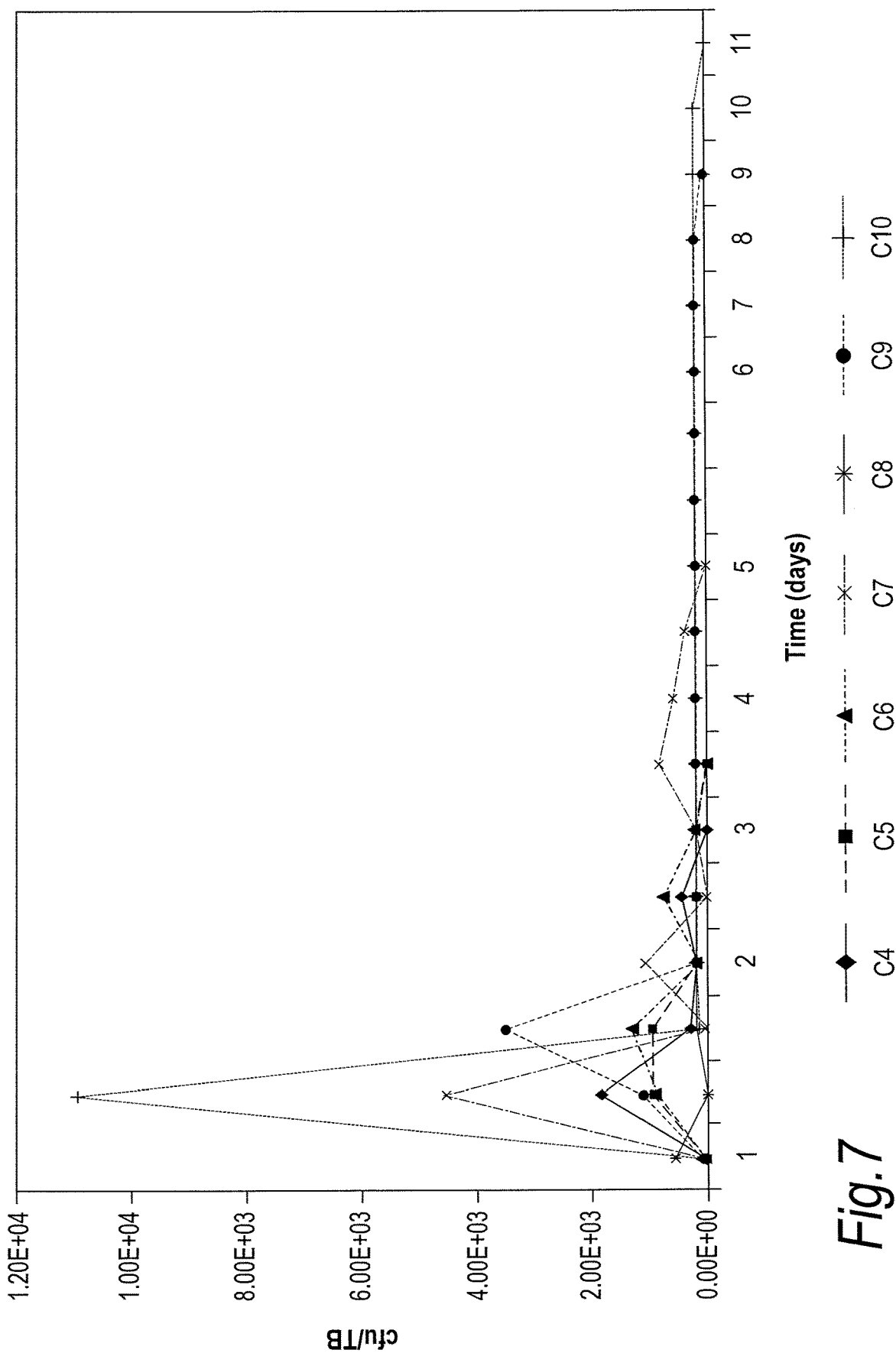
Figure 8:
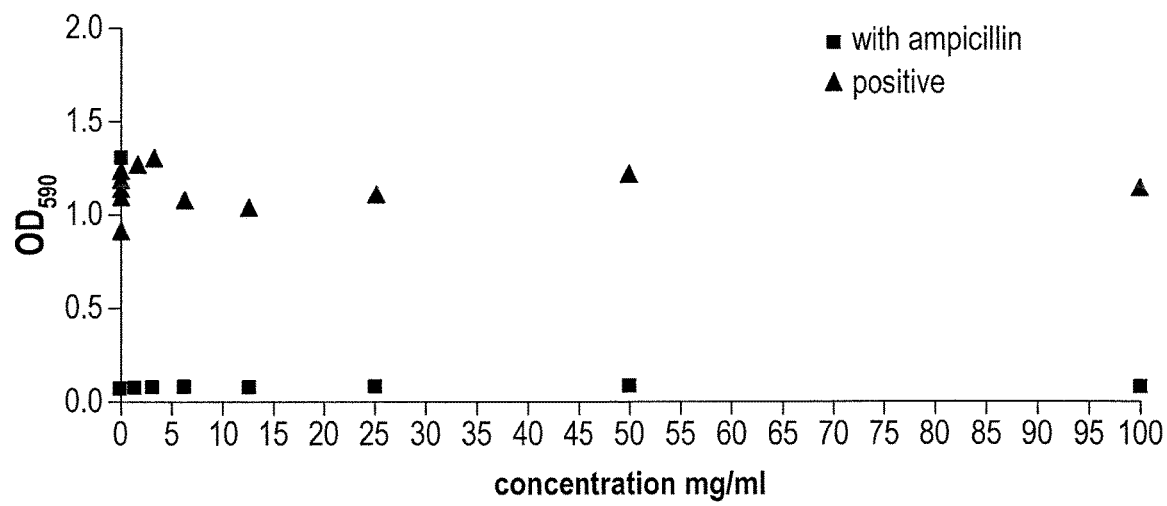
Figure 9:
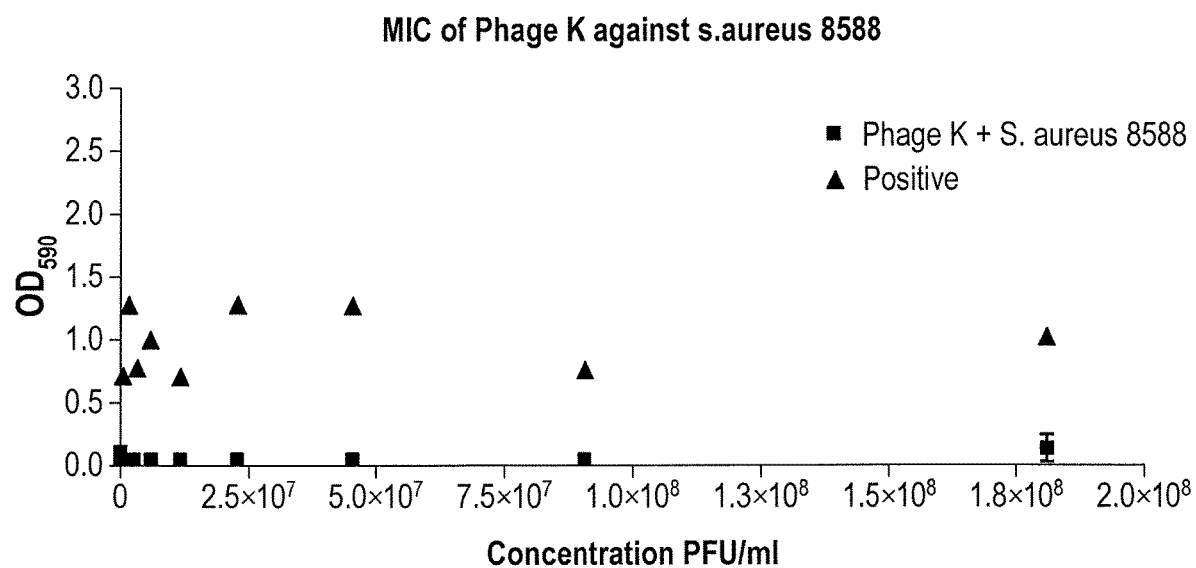
Figure 10:
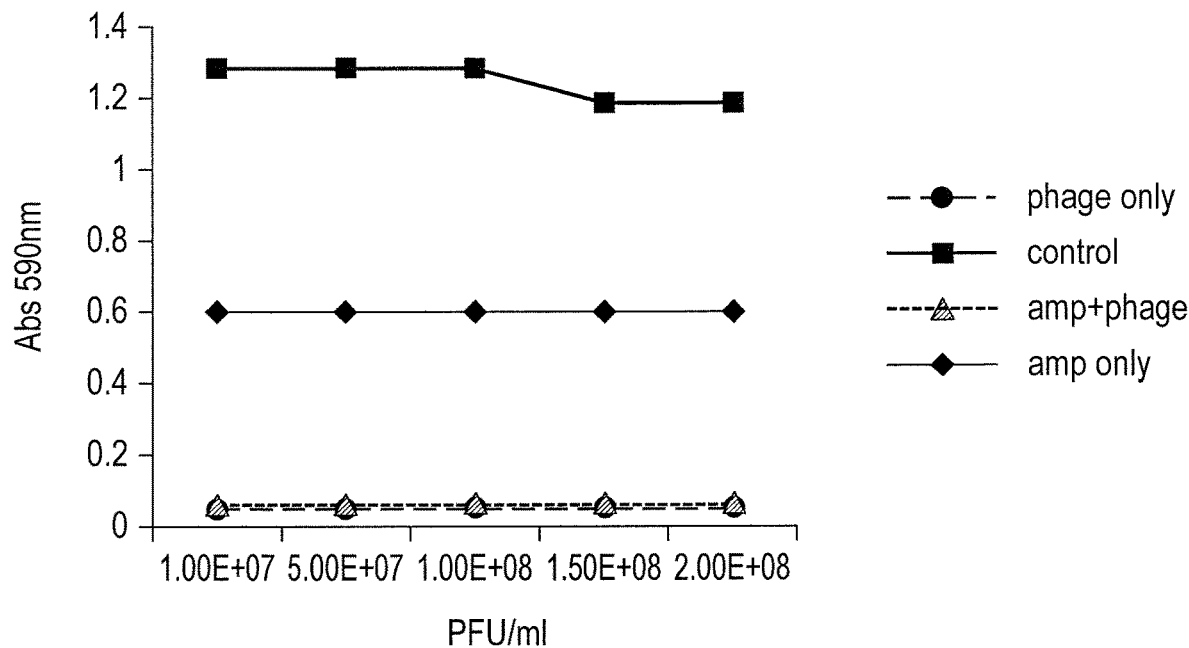
Figure 11:
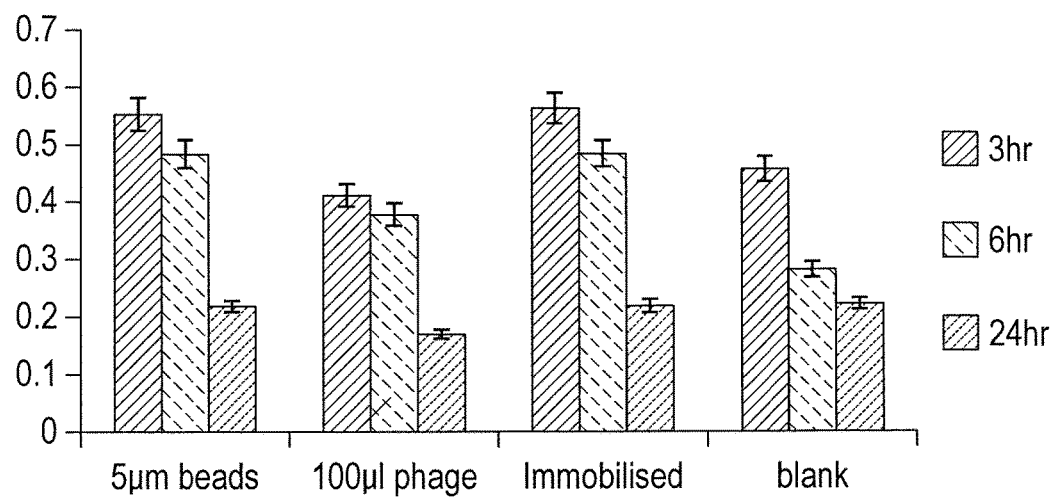
Figure 12:
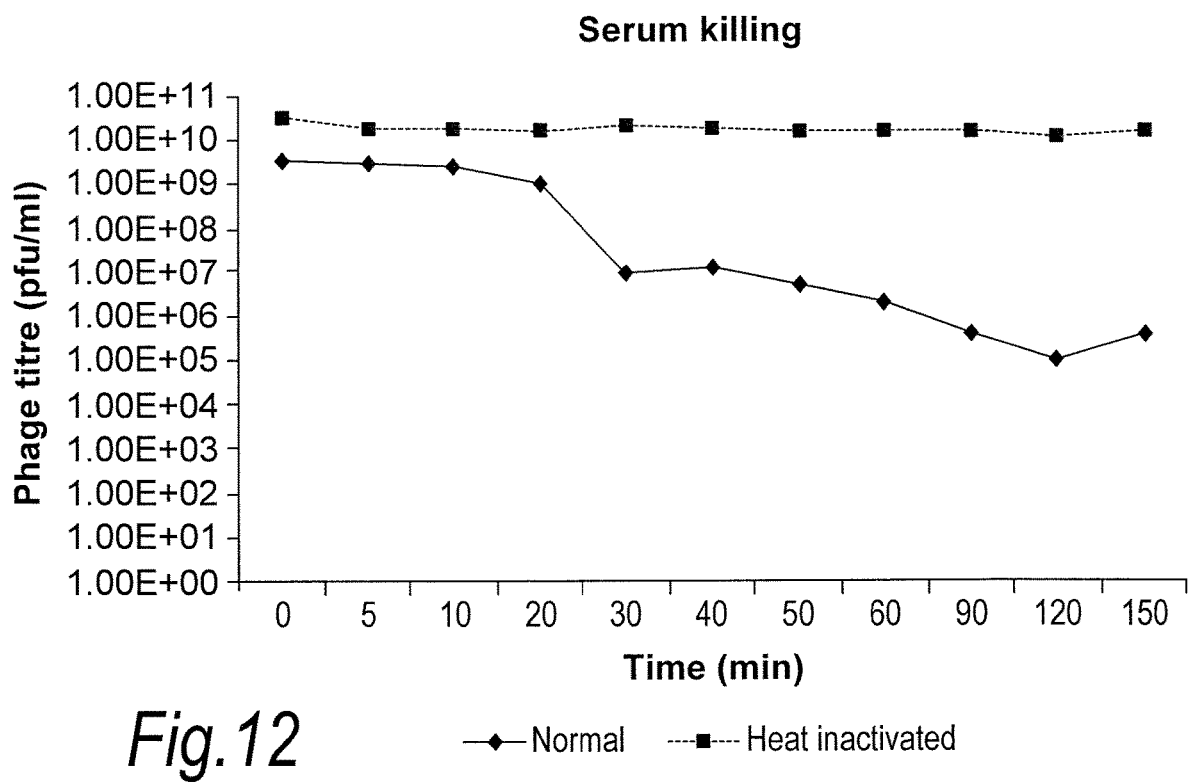
Figure 13:
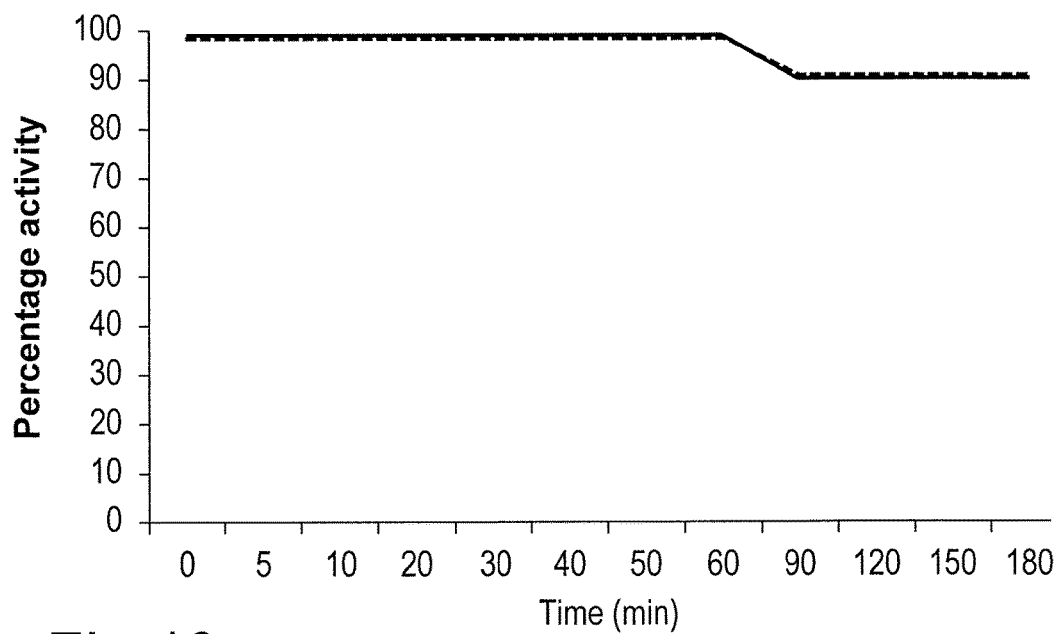
Figure 14:
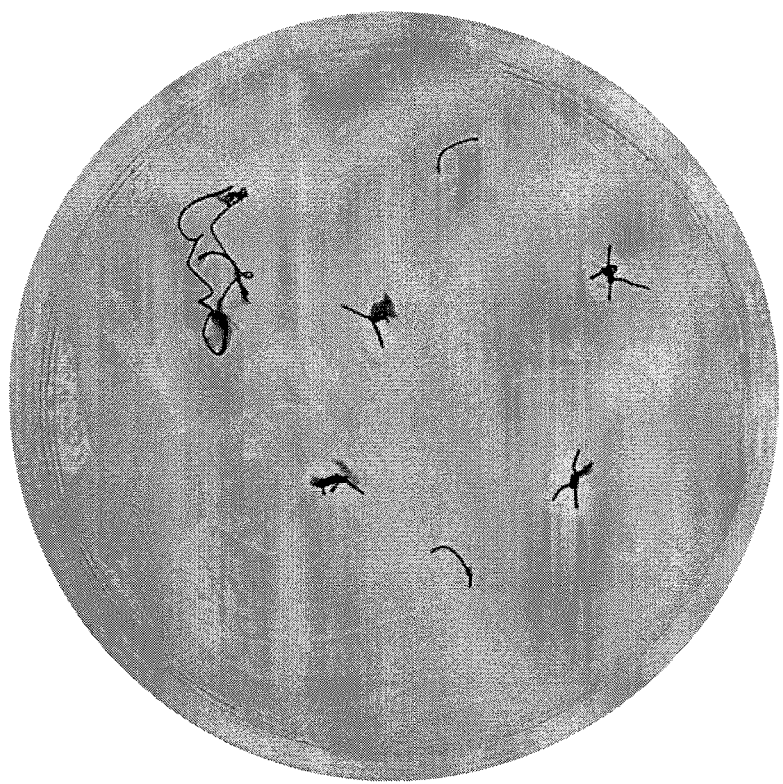
Figure 15:
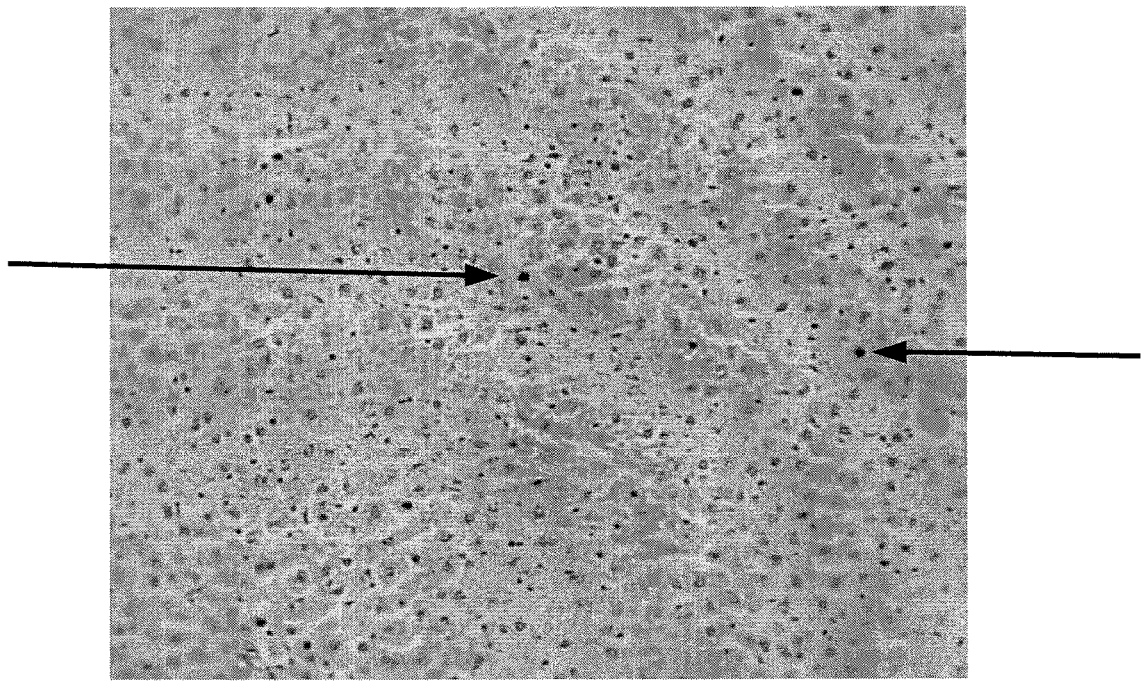
Figure 16:
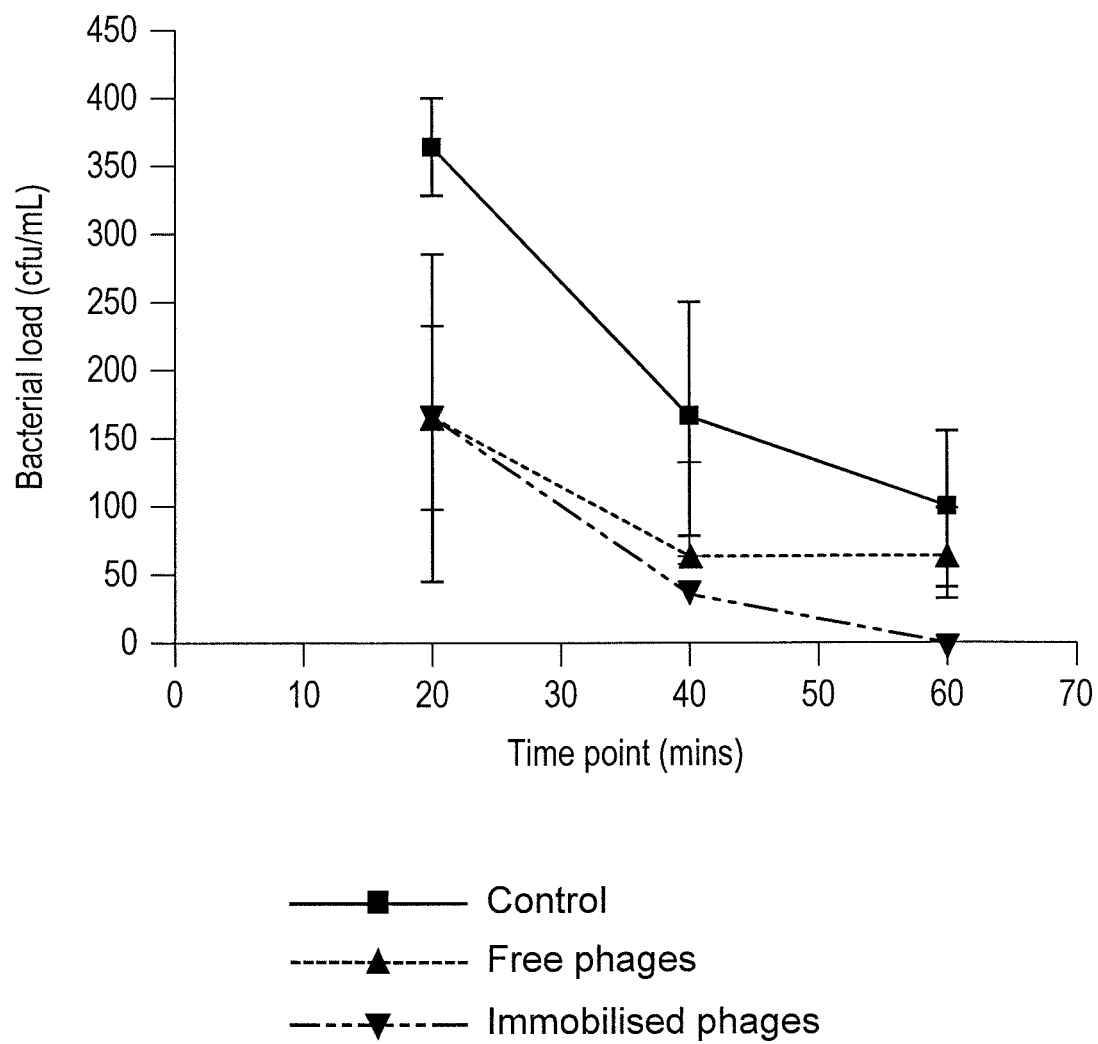

FIG. 6 shows the time course of bacteria in total blood. Test animals (open square, shaded triangle) were inoculated with 50 µl of $5\times10^7$ cfu/ml E15 suspended in 5% hog gastric mucin intraperitoneally (i.p.) with a secondary injection of bacteriophage-treated microspheres intravenously The control animal (shaded diamond) was inoculated with 50 µl of $5\times10^7$ cfu/ml E15 suspended in 5% hog gastric mucin i.p only;

FIG. 7 shows the time course following cfu/total blood in test animals inoculated with 50 µl of $5\times10^7$ cfu/ml E15 suspended in 5% hog gastric mucin i.p with a secondary injection of bacteriophage-treated microspheres i.v.;

FIG. 8 shows the effect of ampicillin on *S. aureus* 8588;

FIG. 9 shows the effect of Phage K on *S. aureus* 8588;

FIG. 10 shows the effect of inhibitory ampicillin concentration on phage K killing of *S. aureus* 8588;

FIG. 11 shows the results of testing an in vivo response to administration of phage on particles;

FIG. 12 shows the effects of normal and heat-inactivated serum on free bacteriophage K;

FIG. 13 shows the effects of normal and heat-inactivated serum on immobilized bacteriophage K;

FIG. 14 shows sutures removed from rat after two weeks;

FIG. 15 shows a photomicrograph of rat liver 14 days after administration of microspheres of the invention; and FIG. 16 shows the results of a trial of phage-containing cream on human skin.

EXAMPLES

Example 1—Bacteriophage Formulations for Acne Treatment

*Propionibacterium acnes* bacteriophages (FP pal) were immobilised onto nylon beads (average diameter 10 microns) and mixed into Formulations A, B and C as set out below. Each Formulation was then tested for survival of bacteriophage at room temperature.

Formulation A—Aqueous Cream
  Anhydrous Lanolin 1.0% w/w
  White Soft Paraffin BP 14.5% w/w
  Light Liquid Paraffin PhEur 12.6% w/w
  Water [to 100%]

Formulation B—Face Wash (Commercially Available Under the Trade Mark "Clearasil")
  Product contents: Aqua, Sodium Gluconate, Propylene Glycol, Octyldodecanol, Steareth-2, Cyclopentasiloxane, Steareth-21, Salicylic Acid, Cetyl Alcohol, Behenyl Alcohol, Cyclohexasiloxane, Polyacrylamide, C13-14 Isoparaffin, Xanthan Gum, Phenoxyethanol, Magnesium Aluminum Silicate, Laureth-7, Menthol, Methylparaben, Butylparaben, Ethylparaben, Isobutylparaben, Propylparaben, CI 77891.

Formulation C—Gel (Commercially Available Under the Trade Mark "Dr Spot")
  Product contents: 2% Salicylic acid, Witch Hazel, Lactic acid.

Resistance to Salicylic Acid
  Formulation A was supplemented with salicylic acid at 0.5, 1.0, 1.5 and 2% w/w, labelled as Formulations A1, A2, A3 and A4. Infectivity of phage in these formulations was compared with infectivity of phage in Formulation A (containing no salicylic acid). After 2 weeks in storage no loss in infectivity was observed in any of A1-A4 compared to the control Formulation A, indicating no adverse effect of the salicylic acid even at 2% on phage survival.

Figure 1:
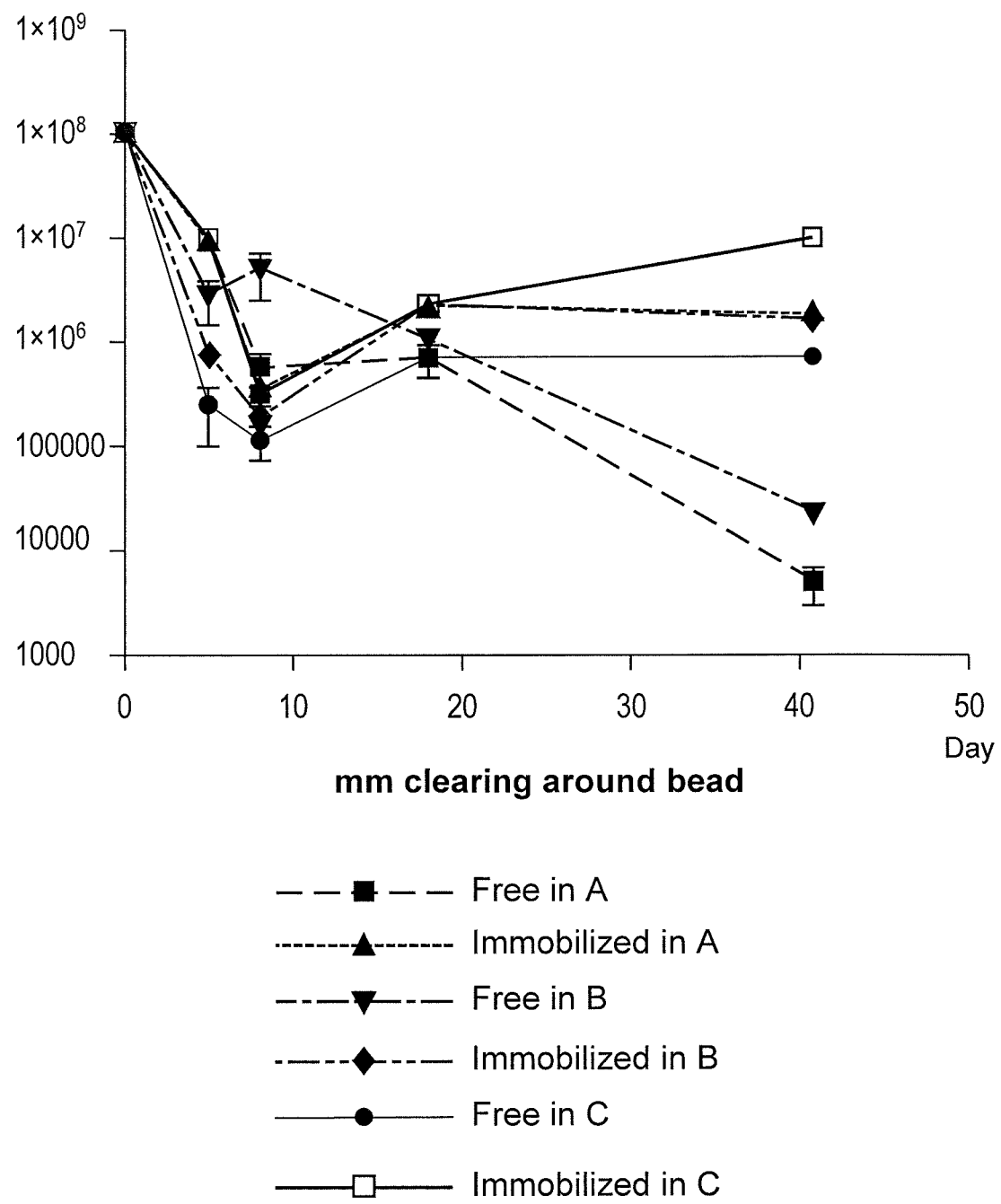

Survival of Phage-Containing Formulations in Storage
  Each of formulations A, B and C were supplemented with *Propionibacterium acnes* bacteriophages covalently immobilised onto nylon 12 particles and the infectivity of the phage compared with the same titre of free (i.e. non-immobilised) phage in the same base formulations. The results over a 6 week period are shown in FIG. 1:
  Hence, phage survival was significantly enhanced by immobilisation onto the nylon particles in each of Formulations A, B and C, in all cases by at least one order of magnitude and in 2 out of 3 by several orders of magnitude.

Example 2—Formulation for Topical Use (S. aureus)

Base Cream Preparation:

120 g of Emulsifying Ointment BP was heated to 60 degrees C. and mixed with 270 ml water also heated to the same temperature. The mixture was carefully stirred as it cooled, producing a smooth, white cream formulation. The cream was cooled to room temperature and divided into 5 equal portions.

Bacteriophage-Particle Production:

Nylon 12 particles of average diameter 3 microns were treated by corona discharge (75 kV field) and rapidly added to a bacteriophage suspension at $1 \times 10^9$ pfu/ml. Particles were washed 3 times to remove non-bound bacteriophages. Using this method, 5 separate 2 ml preparations were made utilizing one of each of 5 different strains of bacteriophage specific for S. aureus from stored phage stock.

Formulation:

To each of the 5 separate portions of cream base was added a separate bacteriophage-particle preparation by admixture and agitation until the suspension had been fully incorporated into the base. The 5 separate bases were then combined and thoroughly mixed to form a single cream base containing 5 different immobilised phage types.

Example 3—Formulation for Topical Use (P. acnes)

A formulation was prepared as follows.
Oil phase: Stearic acid 4%, stearyl alcohol 5%, lanolin 7%, isopropyl myristate 8%.
Aqueous phase: Methyl cellulose 1%, in purified water
The two phases were prepared separately by weight and heated to 70° C. The water phase was then mixed with the oil phase by trituration till the cream congealed and cooled.

Nylon 6,6 particles of average diameter 10 microns were treated by passing through a corona discharge at 70 kv and rapidly added to a mixed bacteriophage preparation containing 5 different bacteriophages against P acnes at a final concentration of $1 \times 10^9$ pfu/ml. The particles were washed 3 times to remove non-bound bacteriophages and added to the cream base to give a final bacteriophage concentration of $1 \times 10^5$ pfu/ml.

Example 4—Treatment of Systemic Infection

Figure 2:
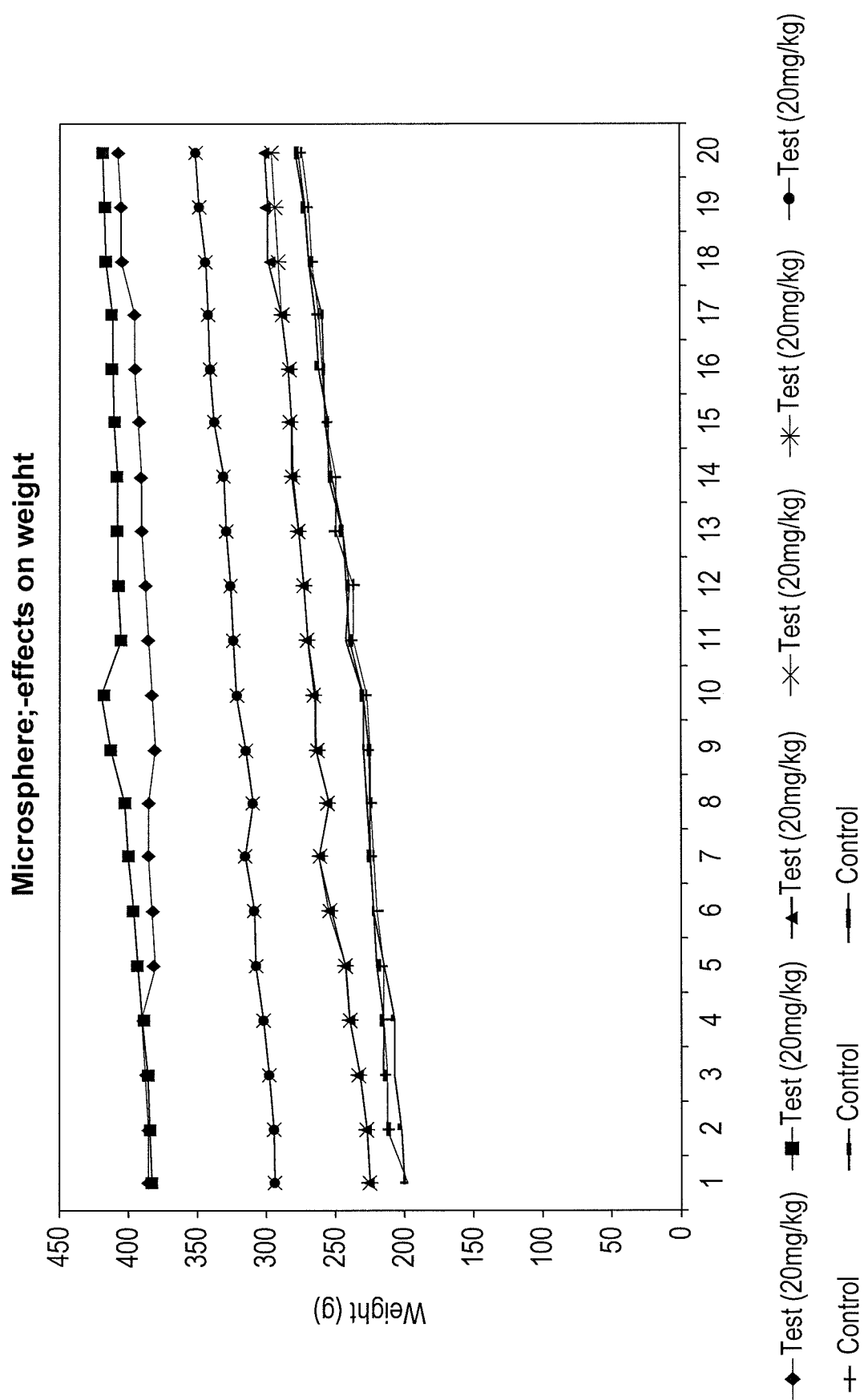
FIG. 2 shows the effect of high dose microspheres treated with purified bacteriophage on weight gain.

Five micron diameter microspheres were prepared by either chemical or corona discharge methods with the addition of the purified bound bacteriophage K. An intravenous (i.v.) injection of 5 µm microspheres suspended in PBS was given to a group of rats at a dose of 20 mg/kg body weight at day 7. There was no change in the weight gain profile, which indicated no significant adverse effect of the microspheres or the immobilised bacteriophages on the animals in the short term—as shown in FIG. 2.

Prior to infection, a temperature transponder was implanted into 2 rats. Body temperature was recorded at intervals of 30 minutes pre-, during and post-infection phase. Animals were handled and weighed over a period of 7 days during which they became accustomed to the restraint process by which blood sampling was be carried out. The experiment used a dose of 100 µl $1 \times 10^8$ cfu/ml EMRSA 15 suspended in 5% hogs gastric mucin using the subcutaneous (s.c.) route as the choice of administration in anaesthetized animals. Injections were given at 09:30 hours, the first sample time point. An i.v. tail injection of 5 µm bacteriophage-treated microspheres was carried out after removal of the tail tip. Numbers of bacteriophages on microspheres were calculated from plaque assays giving a value of $1.1 \times 10^3$ pfu/ml, 100 ul inoculum contained $10^2$ pfu/ml.

Recovery was supervised continuously with blood sampling hourly for 27 hours, then at 6 hourly intervals for the following 3 days. Animals were sacrificed at 14 days post infection during which a final blood sample was taken by cardiac puncture, organs removed, accompanied by blood swabs onto plates and broths to determine the extent of the infection. As microspheres were introduced, organs and blood would also be analysed for the presence of bacteriophage.

Results

Animals recovered fully following a s.c. dose of 100 µl $1 \times 10^8$ cfu/ml E15 and an i.v. tail injection of 5 µm bacteriophage-treated microspheres. The animals showed no clinical signs of distress, and continued in a good general state of health.

Figure 3:
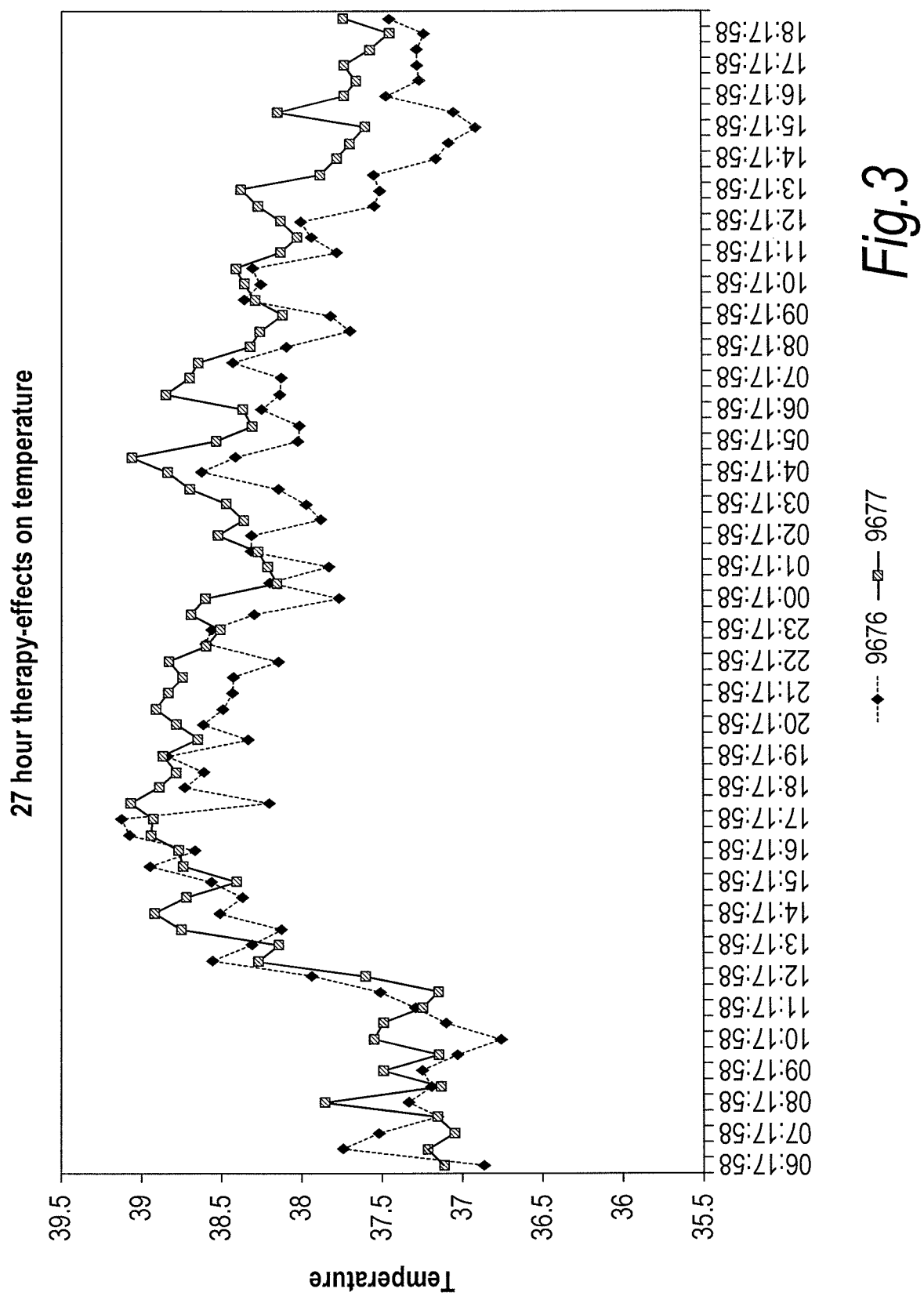
FIG. 3 shows the temperature time course of two animals following a subcutaneous (s.c.) dose of 100 µl $1\times10^8$ cfu/ml E15 and an intravenous (i.v.) tail injection of 5 µm bacteriophage-treated microspheres.

There was a steep rise in temperature which followed shortly after inoculations indicating a fever response in the animal associated with the infection—see FIG. 3. Temperature was maintained at approximately 38.5° C. for 24 hours post inoculation. The bacteriophage bound microspheres at this stage have no direct effect on the temperature when a comparison is made with s.c. injections of bacteria alone.

Figure 4:
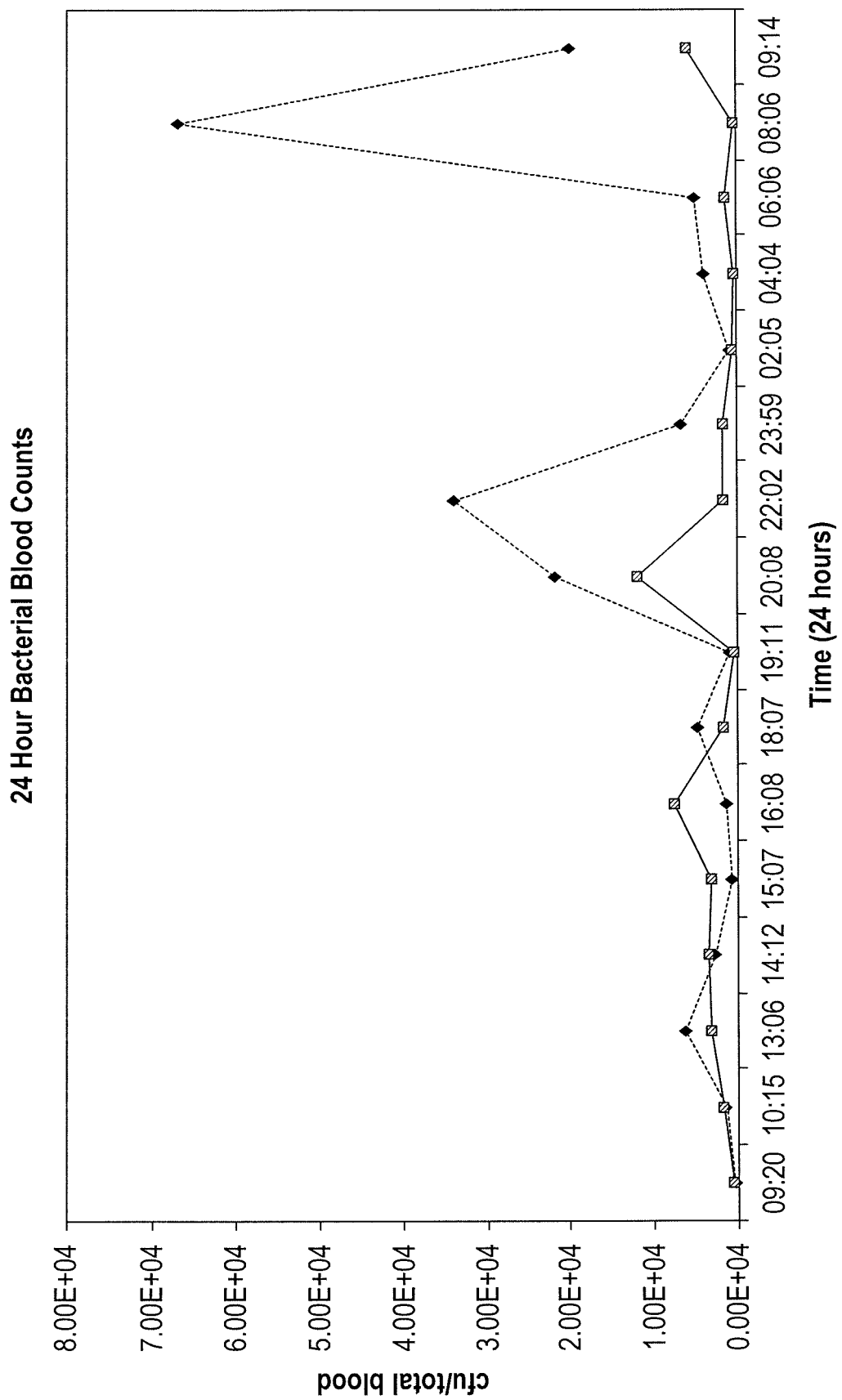
FIG. 4 shows 24 hour bacterial counts following a dose of 100 µl $1\times10^8$ cfu/ml E15 suspended in HM.

Bacterial counts were performed on blood samples—see FIG. 4.

A similar pattern was seen in both animals as the graph indicates that over time, bacterial numbers increased signifying the colonization and influx of bacteria in the animal's body. A correlation was seen between the temperature and the bacterial numbers; a temperature increase coincided with an increase in bacteria in the blood.

Additional universal culture tubes were also filled with L-broth to grow up any bacteria present in the blood. Results reinforced the bacterial counts giving a positive result for each time point. No bacteria were found in the organs following sacrifice 1 week post inoculation indicating the infection had ceased to be systemic.

Blood sampling results demonstrated a relationship between rising bacterial numbers with a raised temperature. However the longevity of this elevated temperature was shown to be affected by the blood sampling procedure itself. No bacteria were found in the blood at sacrifice, 1 week after sampling, which implied that the initial systemic infection had been eliminated.

Figure 5:
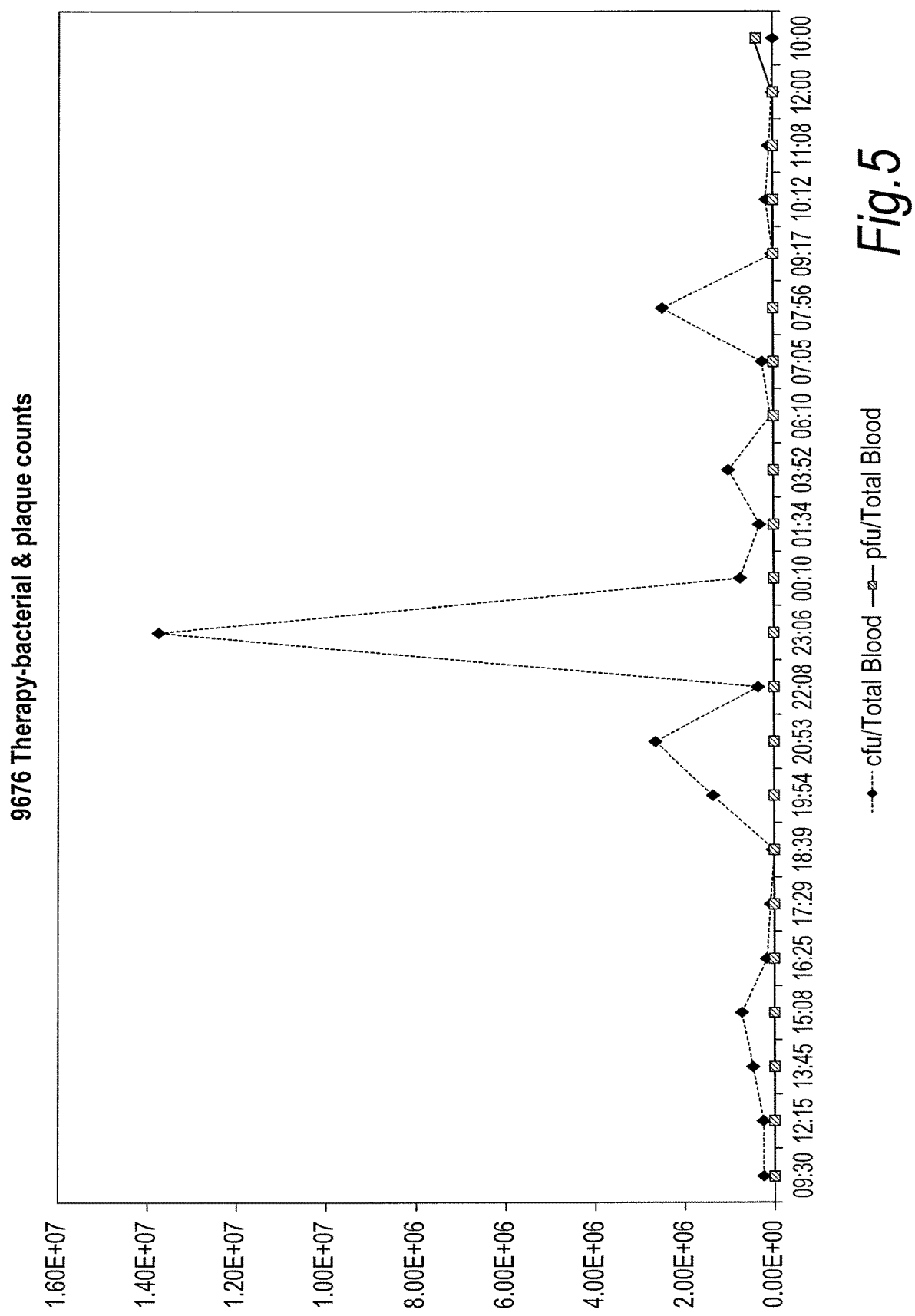
FIG. 5 shows bacterial and bacteriophage time course in one animal (9676) following a s.c. dose of 100 µl $1\times10^8$ cfu/ml E15 and an i.v. tail injection of 5 µm bacteriophage-treated microspheres.

Bacterial counts in organs also gave negative results, which confirms the elimination of the model systemic infection—see FIG. 5; this was in contrast to models where no bacteriophages were introduced when substantial amounts of bacteria were found on sacrifice.

Analysis of the plaques produced on the agar overlay using an inverted microscope did not show the presence of any nylon beads. It was therefore concluded that the bacteriophage isolated were free and not the initial immobilised dose.

We compared bacterial count between treated and control animals—see FIG. 6.

We measured bacterial numbers over 11 days—see FIG. 7. Test animals (C4-C10) showed an initial rise in bacterial numbers in the first two days; however, these figures rapidly declined and were depleted in the subsequent days. This trend was similar in all animals, unlike the continuous rate of bacterial growth seen in the control animals.

We measured bacteriophage numbers in various organs—see Table 1. The results showed that bacterial numbers were significantly lower in all organs than those of bacteriophage. High numbers of free bacteriophage must result from bacterial infection within the animal's body. Their presence in all organs demonstrated the ability of the microspheres or free bacteriophage to travel throughout the body.

TABLE 1

| Organ | cfu/organ | | pfu/organ | |
| --- | --- | --- | --- | --- |
| | animal no. | | | |
| | 9676 | 9677 | 9676 | 9677 |
| Heart | 23 | 0 | 263 | 90 |
| Lung | 0 | 0 | 56 | 127 |
| Spleen | 47 | 22 | 141 | 60 |
| Liver | 859 | 0 | 7 | 23 |
| Kidney | 18 | 0 | 6 | 52 |

(cfu = colony forming units of bacteria; pfu = plaque forming units of bacteriophages)

In the experiments of this example of the invention a relatively low dose of immobilised bacteriophages were used (100) compared with "free" bacteriophages used in experiments reported in the literature (where $10^9$ bacteriophages are often used). The model infection was induced by around $10^6$ bacteria so that bacteria multiplied before bacteriophage numbers rose to a level at which the bacteria were largely eliminated. This is why bacterial numbers continued to increase until 12 to 24 hours after inoculation. The kinetics are complex; bacteria multiply logarithmically but are phagocytosed by the immune system, as well as being infected and destroyed by the bacteriophages. "Free" bacteriophages will also be removed by the immune system (as per the prior art) and immobilised bacteriophages on microbeads as per the invention are now shown to be removed from the circulatory system into the spleen and liver where they remain active (see other data and results herein).

The results showed that:
Nylon microspheres at 5 μm diameter did not cause any obvious adverse effects to the animal
Immobilised bacteriophages in this dose did not cause any measurable adverse effects.
Immobilised bacteriophages infected bacteria in viva
Low doses of immobilised bacteriophages eliminated infecting bacteria in the model.
Free bacteriophages resulted from initial infections with immobilised bacteriophages and the immobilised bacteriophages that do not cause an initial infection remained active.
Both corona treated and chemically treated microbeads were equally active.

Example 5—Formulation Comprising Bacteriophages and Antibiotics

We tested (1) ampicillin, (2) nylon 12 particles onto which bacteriophage K was covalently bound and (3) a formulation in which both were co-administered for effectiveness against S. aureus 8588.

FIG. 8 shows that bacteriophage K was unaffected by the presence of ampicillin at close to MIC concentrations.

The data showed that ampicillin was able to kill the 8588 strain of S. aureus. The MIC of ampicillin against this strain of bacteria was found to be 0.02 mg/ml (20 μg/ml) which showed this to be a resistant strain ("MRSA") (MIC breakpoint 0.125 μg/ml). The absorbance readings of treatments above the MIC were similar to the negative control of Mueller-Hinton broth alone indicating no bacterial growth.

FIG. 9 shows that phage K killed the bacteria 8588 at every concentration. The absorbance readings of the phage K treated wells were similar to the negative control Mueller-Hinton broth alone.

The data in FIG. 10 showed no interaction between ampicillin at 0.01 mg/ml (below MIC) and bacteriophage lysis of S. aureus 8588. The ampicillin value (amp) is from an experiment analogous to that shown in FIG. 8. At 0.01 mg/ml ampicillin (below MIC) the ampicillin has some effect on bacterial growth but is not totally effective as resistant bacteria survive. Addition of phage results in total kill, showing that the phage kills resistant bacteria that would have survived the sub-MIC dose of antibiotic. This showed that resistant bacterial strains that emerge (and would survive if treated only with antibiotic) can be killed by the combination therapy. Hence, co-administration of antibiotic and immobilised phage was effective in killing bacteria in this model.

Example 6—In Vivo Response to Administration of Phage on Particles

P388.D1 cells (mouse lymphoid macrophage cells) were stimulated with (i) 5 micron nylon beads, (ii) 100 microlitres of free phage, (iii) 5 micron beads with phage covalently attached and (iv) a control. Samples were periodically taken and IL-1alpha levels measured using ELISA—see FIG. 11.

A small increase in IL-1alpha was seen after 3 hours stimulation but no effect after 24 hr stimulation. These results indicated the covalently immobilised phage did not induce an immune response in this model.

Example 7—Survival of Immobilised Bacteriophage in Serum

Previous studies (Donlan R. M. (2006) Controlling clinically relevant biofilms using bacteriophage *Biofilm Perspectives* No. 2006:02. www.BiofilmsOnline.com and Sokoloff A., Bock I., Zhang G., Sebestyen M., and Wolff J. (2000) The interaction of peptides with the innate immune system studied with the use of T7 phage peptide display. *Molecular Therapy* 2, 131-139) have shown phages to be inactivated after 3 minutes following contact with serum incubated at 37° C.

An experiment was designed to elucidate whether bacteriophage covalently attached to sutures showed the same effect.

Free phage and phage on sutures were combined with serum ("normal" and heat inactivated), incubated at 37° C. and tested at regular intervals (see results below) for retention of PFU activity.

Results

Referring to FIGS. 12 and 13, it was found that after 10 minutes in the presence of serum the phage titre of free phage was thereafter rapidly reduced. With heat treated serum (in which complement has been inactivated) no loss occurred. Separately, the immobilized phage was resistant to (normal) serum—the phage titre remained stable throughout the experiment. This indicated that the anti-bacteriophage activity of untreated serum is immunologically based.

Example 8

Analysis of Production of IgM and IgG Antibodies Against Immobilised Phage

We investigated the antibody response in rats to administration of phage covalently immobilised onto 5 micron nylon particles. Blood samples were taken by cardiac puncture and serum from these samples was subjected to an ELISA test to determine whether any antibody response could be detected.

Measurement of IgG & IgM by ELISA

Enzyme-linked immunosorbent assay (ELISA) was used to determine whether blood serum contained levels of antibodies to bacteriophage 9563 in experimental rats.

The experiment was performed by the following method: blood was collected from rats at sacrifice and centrifuged at 13,000 rpm for 10 minutes and the resulting serum collected and stored at −20° C. Fresh double-strength coating buffer (100 µl) was added into each well of a 96 well microtitre plate (Greiner Bio-One, Germany) with purified bacteriophage (100 µl) in order to immobilize them to the microplate. PBS (100 µl) was added to control wells and the plate left overnight at 4° C. or for 2 hr at 37° C. The remaining liquid was tipped out and plate was washed thoroughly 3 times with PBS-Tween (Fisher Scientific, Leicestershire, UK). Plates were tapped repeatedly onto paper towels until no liquid remained in the wells. PBS-BSA (10 mg/ml) (200 µl) was added to each well for 0.5 hr at 37° C. to block non-specific binding sites. The remaining liquid was tipped out and the plate was washed thoroughly 3 times with PBS-Tween before 100 µl of serum was added and incubated for 2 hr at room temperature in a sealed box containing wet tissue paper to create a humid atmosphere. Following incubation the remaining liquid was tipped out and the plate washed 3 times with PBS-Tween.

Following washing, 100 µl of a 1 in 1000 dilution of a second antibody of either HRP-mouse anti-Rat IgM, or IgG (Invitrogen, Paisley, UK), was added and the plate incubated at room temperature for 1 hr, or at 37° C. for 30-40 min. The remaining liquid was tipped out and plate was washed 3 times with PBS-Tween. Tetramethyl benzidine (TMB) (150 µl) (Sigma, Aldrich, UK) in acetate citrate buffer (5.2.1.) was added to each well and the plate was incubated at room temperature for 30-40 minutes in the dark, until the reaction mixture turned blue. The reaction was stopped by adding 4M $H_2SO_4$ (50 µl) causing it to turn yellow in colour. Absorbance was read at 450 nm using a plate reader (Labsystems iEMS Reader MF, Finland). Results were compared to control blood samples in which rats were not challenged with phage.

Results

The tables below show the results separately for IgM and IgG. In both cases, there was no statistically significant difference in antibody production—hence the immobilised phage stimulated no production of anti-phage antibodies in the rats tested.

TABLE 2

Statistical analysis of IgM + E15 alone vs IgM E15 + beads & phage
IgM

| Group | IgM + E15 alone | IgM E15 + beads & phage |
|---|---|---|
| Mean | 0.37278200 | 0.26216200 |
| SD | 0.23527212 | 0.24058500 |
| SEM | 0.06074700 | 0.04811700 |
| N | 15 | 25 |

TABLE 3

Statistical analysis of IgG + E15 alone vs IgG E15 + beads & phage
IgG

| Group | IgG + E15 alone | IgG E15 + beads & phage |
|---|---|---|
| Mean | 0.37535700 | 0.31158300 |
| SD | 0.18974907 | 0.16150500 |
| SEM | 0.04899300 | 0.03230100 |
| N | 15 | 25 |

The results showed that the immobilised bacteriophages were poorly immunogenic: there was no immune IgG or IgM response. Repeated subsequent experiments by the inventors, using phage covalently bound to nylon beads, have all consistently shown no detectable antibody response to immobilised phage in rat models.

Example 9—Phage Activity after In Vivo Exposure

Sutures to which phage K were covalently immobilised were prepared and used as per Example 6 in WO2012/175749. At day 14, sutures were removed, washed and their activity tested.

Results

As shown in FIG. 14, the sutures removed after 2 weeks retained phage activity as measured by conventional plaque formation assay. The immobilised phage had not been inactivated by antibodies.

Example 10—In Vivo Retention of Immobilised Phage

Liver samples from rats treated as per example 4 were analyzed 14 days after administration of 5 micron microspheres.

Results

As seen in FIG. 15, microspheres (subsequently confirmed to carry active phage) were detectable (see arrows) in the liver 14 days after systemic administration.

Example 11—Treatment of *P. acnes* on Human Skin

In order to assess the effectiveness of bacteriophage immobilized onto particles on treatment of infection on human skin a short study was undertaken to determine if cream containing bacteriophages would reduce the bacterial load on skin.

Human skin of a volunteer was swabbed with alcohol and inoculated with $1 \times 10^4$ cfu/mL of *P. acnes* (ATCC 6919). This was allowed to air dry and then treated with:
1. E45 cream,
2. E45 cream with $1 \times 10^5$ pfu/g bacteriophage, or
3. E45 cream with $1 \times 10^5$ pfu/g bacteriophages immobilised on approx 10 micron diameter, nylon 12 beads.

At different time points swabs were taken to monitor the quantity of bacteria on the skin.

The results are shown in FIG. 16. As seen, in this study immobilised bacteriophages in a cream base were more effective than free phages and also more effective than the other control (cream alone).

Example 12—Pig Skin as a Model for Skin Infections

We developed the protocol below to use pig skin as a model for human skin infections and treatment thereof according to the invention.

Immobilisation of Bacteriophages

Previously isolated bacteriophages are immobilised onto nylon beads that can be incorporated into acne treatment products; use 10 micron nylon beads, cosmetic grade—as previously described in earlier published work by the applicant e.g. in WO 2007/072049.

System Protocol

The nylon beads act as a model system for immobilisation of bacteriophage to nanoparticles that are to be incorporated into acne treatments and creams.

Each treated material is tested for inhibition of bacterial growth. The effects are compared to material exposed to non-immobilised bacteriophage and material alone. The experiments incorporate multiple tests and continual testing until the inhibitory effect is no longer observed.

Upon completion, the efficacy of immobilised bacteriophage for controlling bacterial growth and the shelf life of immobilised bacteriophage are determined on each material.

Treatment of Skin Infection Using Immobilised Bacteriophages

Pig skin is prepared and inoculated as follows.

Fresh pig skin is handled aseptically. The skin is swabbed with 70% alcohol to remove contaminating bacteria.

Once dry the skin is contaminated with the intended bacterial strain to a concentration of $1 \times 10^4$ cfu/cm$^2$. Using a sterile swab the bacterial solution is smeared into the skin and allowed to air dry in the laminar flow hood for 15 minutes. The desired bacteriophage treatment is applied—using the beads onto which bacteriophage have been immobilised as described above, and the skin then incubated at 37° C. for 16 hours.

The pig skin is assayed for contaminating bacteria on selective media. Bacterial counts are made following inoculation in order to determine if the treatment was successful.

Example 13—Acne Treatment Efficacy on Model Pig Skin

The pig skin model described above was used to demonstrate the efficacy of administration of immobilised bacteriophage for treating acne.

The host bacterium used to inoculate the pig skin was *Staphylococcus aureus* 8588 and the bacteriophage used to infect this bacterium was Phage K.

Phage K were immobilised onto 10 micron diameter nylon beads; $1 \times 10^7$ pfu/mL bacteriophage were immobilised onto 1 g of 10 micron beads.

Pig skin was inoculated with *S. aureus* as described above. The pig skin (4 cm×4 cm) was treated with E45 base cream (1 mL) and approximately $1 \times 10^4$ pfu beads, also as described above.

The results of this test are set out in Table 4 and show that the number of bacteria on the skin test samples was successfully reduced by application of the cream containing immobilised bacteriophages.

TABLE 4

| Test No. | Number of Bacteria (cfu) | | |
|---|---|---|---|
| | Control | Free | Immobilised |
| 1 | 120000 | 150000 | 60000 |
| 2 | 280000 | 170000 | 30000 |
| 3 | 220000 | 180000 | 20000 |
| Mean | 206667 | 166667 | 36667 |

The invention thus provides compositions and methods for treatment of topical and systemic bacterial infections.

The invention claimed is:

1. A method of treating an acne infection of intact skin in a subject in need thereof, comprising administering a topical formulation to the subject, wherein the topical formulation comprises a bacteriophage covalently attached to a carrier particle.

2. The method of claim 1, where in the carrier particle is approximately spherical and has an average diameter of up to 20 microns.

3. The method of claim 1, wherein the treatment is free of salicylic acid and free of benzoyl peroxide.

4. The method of claim 1, wherein the topical formulation comprises bacteriophage active against 3 or more strains of bacteria, wherein the bacteriophage is covalently attached to carrier particles.

5. The method of claim 1, wherein the topical formulation is in the form of a gel, cream, or lotion.

6. The method of claim 5, wherein the topical formulation comprises one or more or all of: a gel-forming agent, a cream-forming agent, a wax, an oil, a surfactant, and a binder.

7. The method of claim 6, wherein the topical formulation comprises carrier particles with an average diameter of up to 20 microns.

8. The method of claim 7, wherein the topical formulation comprises carrier particles with an average diameter of up to 10 microns.

9. The method of claim 1, wherein the topical formulation comprises bacteriophages lytic for *P. acnes* covalently attached to the carrier particles with an average diameter of up to 20 microns, wherein the topical formulation is in the form of a cream or a gel.

10. The method of claim 9, wherein the topical formulation comprises bacteriophages lytic for at least 3 different strains of *P. acnes*, wherein the bacteriophages are covalently attached to the carrier particles.

11. The method of claim 1, wherein the topical formulation comprises bacteriophages lytic for *S. aureus* covalently attached to carrier particles with an average diameter of up to 20 microns, wherein the formulation is in the form of a cream or a gel.

12. The method of claim 11, wherein the topical formulation comprises bacteriophages lytic for at least 3 different strains of *S. aureus* covalently attached to the carrier particles.

* * * * *